United States Patent
Galitsky

(10) Patent No.: US 12,106,054 B2
(45) Date of Patent: Oct. 1, 2024

(54) MULTI CASE-BASED REASONING BY SYNTACTIC-SEMANTIC ALIGNMENT AND DISCOURSE ANALYSIS

(71) Applicant: Oracle International Corporation, Redwood Shores, CA (US)

(72) Inventor: Boris Galitsky, San Jose, CA (US)

(73) Assignee: Oracle International Corporation, Redwood Shores, CA (US)

( * ) Notice: Subject to any disclaimer, the term of this patent is extended or adjusted under 35 U.S.C. 154(b) by 360 days.

(21) Appl. No.: 17/207,465

(22) Filed: Mar. 19, 2021

(65) Prior Publication Data
US 2022/0114346 A1   Apr. 14, 2022

Related U.S. Application Data

(60) Provisional application No. 63/090,620, filed on Oct. 12, 2020.

(51) Int. Cl.
*G06F 40/35* (2020.01)
*G06F 40/205* (2020.01)

(52) U.S. Cl.
CPC ............ *G06F 40/35* (2020.01); *G06F 40/205* (2020.01)

(58) Field of Classification Search
None
See application file for complete search history.

(56) References Cited

U.S. PATENT DOCUMENTS

| | | | |
|---|---|---|---|
| 11,301,502 B1 * | 4/2022 | Dijamco | G06F 40/35 |
| 2005/0154616 A1 * | 7/2005 | Liff | G16H 15/00 |
| | | | 705/3 |

(Continued)

FOREIGN PATENT DOCUMENTS

| | | | |
|---|---|---|---|
| CN | 109166619 A | * 1/2019 | |
| WO | WO-2018208979 A1 | * 11/2018 | ........... G06F 16/322 |

OTHER PUBLICATIONS

Boris Galitsky; Dmitry Ilvovsky, Building Dialogue Structure from Discourse Tree of a Question, Oct. 31, 2018, Association for Computational Linguistics, https://aclanthology.org/W18-5703/ (Year: 2018).*

(Continued)

*Primary Examiner* — Daniel C Washburn
*Assistant Examiner* — Oluwadamilola M Ogunbiyi
(74) *Attorney, Agent, or Firm* — Kilpatrick Townsend & Stockton LLP

(57) ABSTRACT

Systems, devices, and methods discussed herein provide improved autonomous agent applications that are configured to generate a diagnosis for input symptoms from labels (e.g., diseases, illnesses, and/or conditions) associated with previously-known cases. Extended discourse trees may be generated that identify multiple discourse trees corresponding to various fragment granularities (e.g., document, paragraph, sentence, phrase, word, etc.) of previously-known cases as well as rhetorical relations between those discourse trees. New symptoms can be provided (e.g., via the autonomous agent) as input. The input can be parsed to identify various fragments of the input and rhetorical relations between the fragments. These fragments can be matched to fragments of previously-known cases by matching nodes of the extended discourse tree. If the rhetorical relations between the input fragments match the rhetorical relations indicated in the extended discourse tree of a previously-known cases, the input may be classified with the same label as those previously-known cases.

20 Claims, 12 Drawing Sheets

(56) References Cited

U.S. PATENT DOCUMENTS

| | | | | |
|---|---|---|---|---|
| 2010/0228693 | A1* | 9/2010 | Dawson | G06F 40/30 |
| | | | | 707/769 |
| 2015/0051900 | A1* | 2/2015 | Kimelfeld | G06F 40/211 |
| | | | | 704/9 |
| 2016/0364476 | A1* | 12/2016 | Curin | G06F 40/268 |
| 2018/0365593 | A1* | 12/2018 | Galitsky | G06F 16/36 |
| 2019/0221313 | A1* | 7/2019 | Rim | G06F 18/217 |
| 2019/0236085 | A1* | 8/2019 | Galitsky | G06N 5/022 |
| 2019/0236134 | A1* | 8/2019 | Galitsky | G06F 40/131 |
| 2020/0060566 | A1* | 2/2020 | Howard | A61B 5/4824 |
| 2020/0210268 | A1* | 7/2020 | Nuthi | G06F 11/0751 |
| 2020/0401938 | A1* | 12/2020 | Etkin | G06N 5/022 |
| 2021/0027133 | A1* | 1/2021 | Ludwig | G06F 18/24 |
| 2021/0035661 | A1* | 2/2021 | Neumann | G16H 20/00 |
| 2021/0050076 | A1* | 2/2021 | Wachira | G16H 50/20 |
| 2021/0169417 | A1* | 6/2021 | Burton | A61B 5/4857 |
| 2021/0174030 | A1* | 6/2021 | Galitsky | G06F 40/279 |
| 2021/0232613 | A1* | 7/2021 | Raval Contractor | G06N 5/02 |
| 2022/0138432 | A1* | 5/2022 | Galitsky | G06F 40/211 |
| | | | | 704/9 |
| 2022/0215174 | A1* | 7/2022 | Galitsky | G06F 40/295 |
| 2022/0318517 | A1* | 10/2022 | Galitsky | G06F 40/35 |

OTHER PUBLICATIONS

Boris Galitsky; Dmitry Ilvovsky, Chatbot with a Discourse Structure-Driven Dialogue Management, Apr. 7, 2017, Association for Computational Linguistics, https://aclanthology.org/E17-3022/ (Year: 2017).*

Boris Galitsky, Machine Learning of Syntactic Parse Trees for Search and Classification of Text, Nov. 13, 2012, Elsevier Ltd., https://www.sciencedirect.com/science/article/pii/S0952197612002552 (Year: 2012).*

Marcu, Daniel. "The rhetorical parsing of unrestricted texts: A surface-based approach." Computational linguistics 26.3 (2000): 395-448. (Year: 2000).*

Galitsky, Boris. "Matching parse thickets for open domain question answering." Data & Knowledge Engineering 107 (2017): 24-50. (Year: 2017).*

Galitsky, Boris. "Discovering rhetoric agreement between a request and response." Dialogue & Discourse 8.2 (2017): 167-205. (Year: 2017).*

Burstein, Jill, Daniel Marcu, and Kevin Knight. "Finding the WRITE stuff: Automatic identification of discourse structure in student essays." IEEE Intelligent Systems 18.1 (2003): 32-39. (Year: 2003).*

International Classification of Diseases, ICD-11, 11th Revision, Available Online at: https://icd.who.int/en, 2020, 2 pages.

Swollen Lymphs Nodes in Neck and Collarbone, Haematological Disorders, PatientInfo, Available Online at: https://patient.info/forums/discuss/swollen-lymphsnodes-in-neck-and-collarbone-734682, 2020, 3 pages.

Aamodt et al., Case-Based Reasoning: Foundational Issues, Methodological Variations, and System Approaches, AI Communications. IOS Press, vol. 7, No. 1, 1994, pp. 39-59.

Ahmed et al., A Multi-Module Case-based Biofeedback System for Stress Treatment, Artificial Intelligence in Medicine, vol. 51, No. 2, Feb. 2011, pp. 107-115.

Ahn et al., Global Optimization of Case-based Reasoning for Breast Cytology Diagnosis, Expert Systems with Applications, vol. 36, No. 1, Available Online at: 10.1016/j.eswa.2007.10.023, Jan. 2009, pp. 724-734.

Balogh et al., Improving Diagnosis in Health Care, Committee on Diagnostic Error in Health Care; Board on Health Care Services; Institute of Medicine; The National Academies of Sciences, Engineering, and Medicine., Dec. 29, 2015.

Branting et al., Dialogue Management for Conversational Case-Based Reasoning, LiveWire Logic, Inc., 15 pages.

Choudhury et al., A Survey on Case-based Reasoning in Medicine, International Journal of Advanced Computer Science and Applications (IJACSA), vol. 7, No. 8, 2016, pp. 136-144.

Das, A Machine Learning Model for Detecting Respiratory Problems Using Voice Recognition, Institute of Electrical and Electronics Engineers 5th International Conference for Convergence in Technology (I2CT), Mar. 29-31, 2019, pp. 1-3.

Dayanand et al., GRAph ALigner: Algorithm to Align Two Networks or Graphs, Available Online at: https://github.com/kanthkumar46/GRAAL, 2018, 2 pages.

De Boom et al., Learning Semantic Similarity for Very Short Texts, Institute of Electrical and Electronics Engineers International Conference on Data Mining Workshop (ICDMW), Nov. 14-17, 2015, 6 pages.

Flanigan et al., A Discriminative Graph-based Parser for the Abstract Meaning Representation, Proceedings of the 52nd Annual Meeting of the Association for Computational Linguistics, Jun. 2014, pp. 1426-1436.

Galitsky et al., Chatbot with a Discourse Structure-Driven Dialogue Management, Proceedings of the Software Demonstrations of the 15th Conference of the European Chapter of the Association for Computational Linguistics, Apr. 3-7, 2017, pp. 87-90.

Galitsky et al., Finding Maximal Common Sub-Parse Thickets for Multi-Sentence Search, Graph Structures for Knowledge Representation and Reasoning, 2014, 19 pages.

Galitsky et al., Inferring the Semantic Properties of Sentences by Mining Syntactic Parse Trees, Data & Knowledge Engineering, vols. 81-82, Available Online at: http://dx.doi.org/10.1016/j.datak.2012.07.003.2012, Nov.-Dec. 2012, 44 pages.

Galitsky, Machine Learning of Syntactic Parse Trees for Search and Classification of Text, Engineering Applications of Artificial Intelligence, vol. 26, Available Online at: http://dx.doi.org/10.1016/j.engappai.2012.09.017, Mar. 2013, pp. 1072-1091.

Galitsky, Matching Parse Thickets for Open Domain Question Answering, Data & Knowledge Engineering, vol. 107, Dec. 9, 2016, pp. 24-50.

Galitsky et al., Using Generalization of Syntactic Parse Trees for Taxonomy Capture on the Web, Proceedings of the 19th International Conference on Conceptual Structures for Discovering Knowledge, Jul. 25-29, 2011, pp. 104-117.

Gu et al., Intelligent Technique for Knowledge Reuse of Dental Medical Records Based on Case-based Reasoning, Journal of Medical Systems, vol. 34, No. 2, Available Online at: 10.1007/s10916-008-9232-y, Apr. 2010, pp. 213-222.

Gupta et al., Data Mining Classification Techniques Applied for Breast Cancer Diagnosis and Prognosis, Indian Journal of Computer Science and Engineering (IJCSE), vol. 2, No. 2, April-May 2011, pp. 188-195.

Holt et al., Medical Applications in Case-based Reasoning, The Knowledge Engineering Review, vol. 20, No. 3, Sep. 2005, pp. 289-292.

Galitsky et al., Matching Sets of Parse Trees for Answering Multi-Sentence Questions, Proceedings of Recent Advances in Natural Language Processing, Hissar, Bulgaria, Sep. 7-13, 2013, pp. 285-293.

Liu et al., Thread Structure Learning on Online Health Forums with Partially Labeled Data, Institute of Electrical and Electronics Engineers Transactions on Computational Social Systems, vol. 6, No. 6, Available Online at: 10.1109/TCSS.2019.2946498, Dec. 2019, pp. 1273-1282.

Marling et al., Toward Case-based Reasoning for Diabetes Management: a Preliminary Clinical Study and Decision Support System Prototype, Computational Intelligence, vol. 25, No. 3, Available Online at: 10.1111/j.14678640.2009.00336.x., 2009, pp. 165-179.

Milenkovic et al., Optimized Null Model for Protein Structure Networks, PLoS One, vol. 4, No. 6, Jun. 2009, 9 pages.

Nnebe et al., A Neuro-Fuzzy Case Based Reasoning Framework for Detecting Lassa Fever Based on Observed Symptoms, American Journal of Artificial Intelligence, vol. 3, No. 1, Available Online at: 10.11648/j.ajai.20190301.12, Jun. 2019, pp. 9-16.

(56) References Cited

OTHER PUBLICATIONS

Ocampo et al., Comparing Bayesian Inference and Case-based Reasoning as Support Techniques in the Diagnosis of Acute Bacterial Meningitis, Expert Systems with Applications, vol. 38, No. 8, Aug. 2011, pp. 10343-10354.

Pourdamghani et al., Aligning English Strings with Abstract Meaning Representation Graphs, Empirical Methods in Natural Language Processing (EMNLP), Oct. 25-29, 2014, pp. 425-429.

Przulj, Biological Network Comparison Using Graphlet Degree Distribution, Bioinformatics, vol. 23, No. 2, Jan. 15, 2007, pp. e177-e183.

Rose et al., Discourse Processing of Dialogues with Multiple Threads, Proceedings of the 33rd Annual Meeting of the Association for Computational Linguistics, Apr. 27, 1995, pp. 31-38.

Schmidt et al., Cased-based Reasoning for Medical Knowledge-based Systems, International Journal of Medical Informatics, vol. 64, Nos. 2-3, Dec. 2001, pp. 355-367.

Schmidt et al., Experiences with Case-based Reasoning Methods and Prototypes for Medical Knowledge-based Systems, Joint European Conference on Artificial Intelligence in Medicine and Medical Decision Making, Artificial Intelligence in Medicine, vol. 1620, Jun. 11, 1999, pp. 124-132.

Seo et al., Online Community Search Using Thread Structure, In Proceedings of the 18th ACM Conference on Information and Knowledge Management, Nov. 2009, pp. 1907-1910.

Sheth et al., Active Semantic Electronic Medical Record, International Semantic Web Conference, The Semantic Web—ISWC 2006, 2006, pp. 913-926.

Supekar et al., Fuzzy Rule-based Framework for Medical Record Validation, International Conference on Intelligent Data Engineering and Automated Learning, Intelligent Data Engineering and Automated Learning, vol. 2412, 2002, pp. 1-27.

Takemura et al., A Study of the Medical Record Interface to Natural Language Processing, Journal of Medical Systems, vol. 26, No. 2, Available Online at: 10.1023/A:1014866123819, Apr. 2002, pp. 79-87.

Ting et al., A Hybrid Knowledge-based Approach to Supporting the Medical Prescription for General Practitioners: Real Case in a Hong Kong Medical Center, Knowledge-Based Systems, vol. 24, No. 3, Apr. 2011, pp. 444-456.

Wang et al., Semantic-Enhanced Case-Based Reasoning for Intelligent Recommendation, WRI World Congress on Computer Science and Information Engineering, vol. 5, Mar. 31-Apr. 2, 2009, pp. 697-701.

\* cited by examiner

300

```
elaboration
  elaboration
    temporal_sequence
      explanation
        TEXT:I experience fatigue and hunger,
        elaboration
          TEXT:because I do not acquire enough energy from the meals
          TEXT:I eat.
      joint
        TEXT:I urinate
        TEXT:and feel thirsty fairly frequently.
    elaboration
      elaboration
        TEXT:I lack a sharpness of vision
        enablement
          TEXT:resulting in the inability
          TEXT:to see fine detail.
      TEXT:Later I started feel tingling in the hands and feet .
    elaboration
      elaboration
        elaboration
          TEXT:After that, I feel numbness, pain and burning sensations
          TEXT:starting in the toes and fingers then continuing up the legs or arms
          cause
            TEXT:I lost loss of muscle tone in my hands and feet, as well as a loss of balance.
            TEXT:As a result, I started feeling fatigue, pale skin, chest pain and irregular heartbeat.
        elaboration
          TEXT:I noticed blood in urine,
          TEXT: which is now dark, a drop in mental alertness and itchy skin.
```

- 302: explanation block (fatigue, hunger, urinate, thirsty)
- 304: vision block (sharpness, tingling)
- 306: later symptoms block (numbness, muscle tone, blood in urine)

FIG. 3

MULTI CASE-BASED REASONING BY SYNTACTIC-SEMANTIC ALIGNMENT AND DISCOURSE ANALYSIS

CROSS-REFERENCE TO RELATED APPLICATIONS

This non-provisional application claims priority to U.S. Patent Application No. 63/090,620, filed on Oct. 12, 2020, entitled "Multi Case-Based Reasoning by Syntactic-Semantic Alignment and Discourse Analysis," the disclosure of which is herein incorporated by reference in its entirety for all purposes.

TECHNICAL FIELD

This disclosure is generally concerned with linguistics. More specifically, this disclosure relates to using providing automated answers to questions using multi-case-based reasoning through syntactic-semantic alignment and discourse analysis.

BACKGROUND

Linguistics is the scientific study of language. One aspect of linguistics is the application of computer science to human natural languages such as English. Due to the greatly increased speed of processors and capacity of memory, computer applications of linguistics are on the rise. For example, computer-enabled analysis of language discourse facilitates numerous applications such as automated agents that can answer questions from users. The use of "chatbots" and agents to answer questions, facilitate discussion, manage dialogues, and provide social promotion is increasingly popular. To address this need, a broad range of technologies including compositional semantics has been developed. Such technologies can support automated agents in the case of simple, short queries and replies.

BRIEF SUMMARY

Aspects of the present disclosure relate to utilizing multiple previously-classified cases (including one or more documents) for classifying input. In at least one embodiment, a method is disclosed for providing textual output (e.g., a diagnosis classification label) in response to textual input (e.g., user-provided symptoms, a medical record, etc.). The method may comprise obtaining, by one or more processors, a set of document fragments of a corpus of documents, each document fragment being associated with one or more classification labels identifying a topic of the document fragment. The method may further comprise obtaining, by the one or more processors, a plurality of extended discourse trees. In some embodiments, each of the extended discourse trees identifies relationships between a subset of document fragments from the set of document fragments. In some embodiments, each extended discourse tree includes at least two discourse trees, each discourse tree including a plurality of nodes, each nonterminal node representing a rhetorical relationship between at least two fragments of a corresponding document. In some embodiments, the extended discourse tree indicates one or more rhetorical relationships between the corresponding fragments of the at least two discourse trees, and each terminal node of the nodes of the discourse tree being associated with one of the fragments. The method may further comprise receiving textual input for a search by the one or more processors. The method may further comprise generating, by the one or more processors, a discourse tree from the textual input. In some embodiments, the discourse tree represents rhetorical relationships between one or more portions of the textual input. The method may further comprise matching, by the one or more processors, one or more subtrees of the discourse tree from the textual input and one or more subtrees of the plurality of extended discourse trees. The method may further comprise identifying a corresponding classification label for each of the fragments of the textual input based at least in part on the matching. The method may further comprise classifying the textual input as being associated with the corresponding classification label. The method may further comprise providing textual output corresponding to the textual input and including the classification label.

In some embodiments, the method may further comprise parsing the textual input to generate an abstract meaning representation of the textual input, the abstract meaning representation comprising a directed acyclic graph including a plurality of nodes and edges, the nodes representing discourse units of the textual input and the edges specifying semantic relationships between the nodes. The method may further comprise determining, by the one or more processors, using an extended discourse tree associated with the set of document fragments and the abstract meaning representation of the input, that the relationships between the fragments of the set of documents agree with the semantic relationships indicated by the abstract meaning representation of the textual input.

In some embodiments, the textual input is classified in response to determining that the relationships between the fragments of the set of documents agree with the semantic relationships indicated by the abstract meaning representation of the input.

In some embodiments, the extended discourse trees are generated based at least in part on generating a respective discourse tree for each of the set of document fragments, identifying relations between respective pairs of discourse trees, and generating a link between the respective pairs of discourse trees identifying the relations between the respective pairs of discourse trees.

In some embodiments, the plurality of extended discourse trees identify the relationships between the subset of document fragments from the set of document fragments based at least in part on at least one of: a word level, a phrase level, a paragraph level, a sentence level, or a document level.

In some embodiments, the set of documents fragments individually describe symptoms of a respective medical condition.

In some embodiments, the textual input is narrative or structured content from a user's medical file.

In at least one embodiment, a computing device is disclosed. The computing device may comprise a computer-readable medium storing non-transitory computer-executable program instructions and a processing device communicatively coupled to the computer-readable medium for executing the non-transitory computer-executable program instructions. In some embodiments, executing the non-transitory computer-executable program instructions with the processing device causes the computing device to perform the method disclosed above.

In at least one embodiment, a non-transitory computer-readable storage medium storing computer-executable program instructions for generating an automated answer to a question is disclosed. In some embodiments, executing the program instructions by one or more processors of a computing device, cause the computing device to perform the method disclosed above.

BRIEF DESCRIPTION OF THE DRAWINGS

FIG. 3 is a block diagram depicting an example discourse tree generated from user input, in accordance with at least one embodiment.

DETAILED DESCRIPTION

Figure 1:
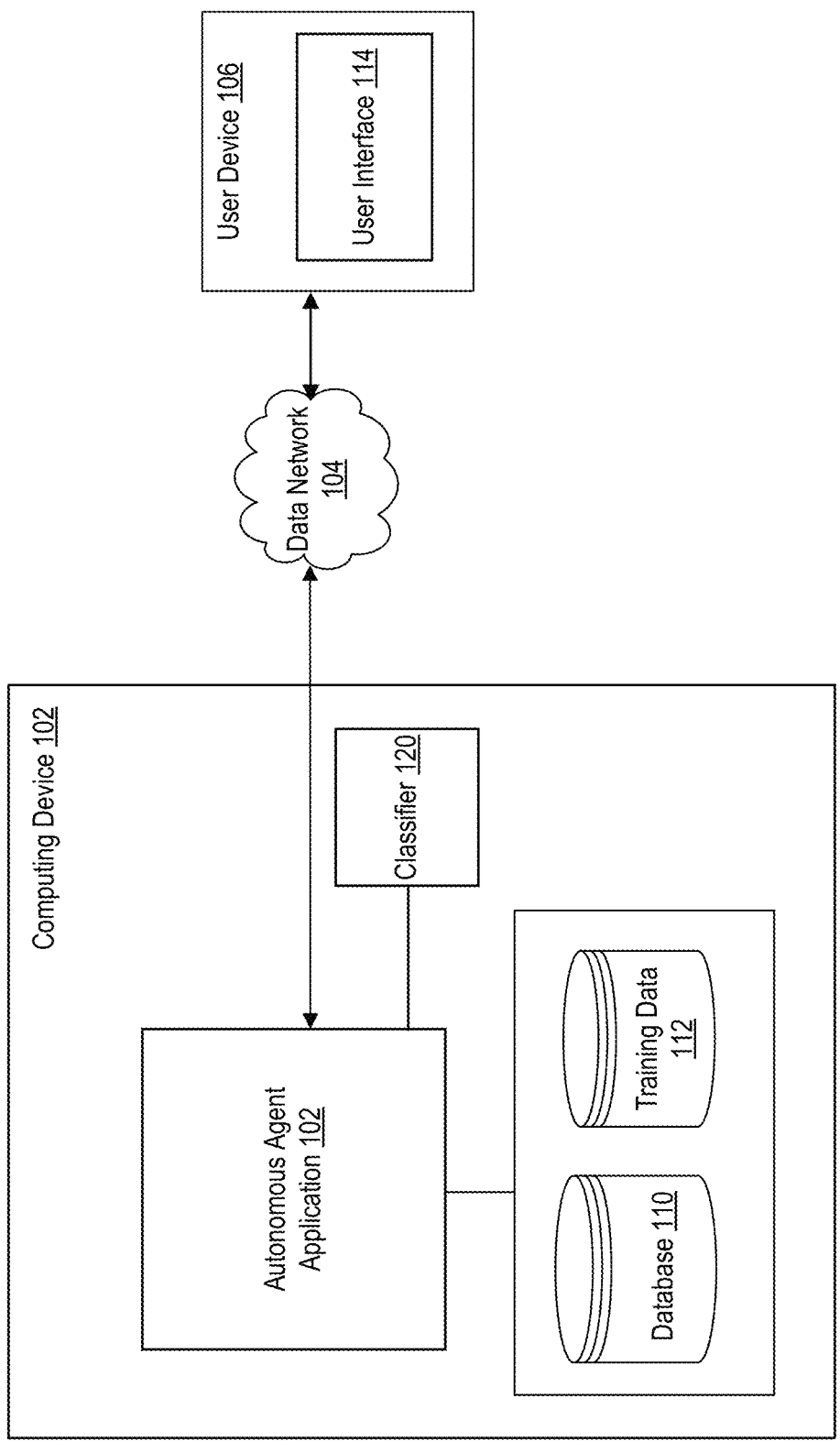
FIG. 1 depicts autonomous agent environment, in accordance with at least one embodiment.

Aspects of the present disclosure relate to generating automated answers for medical questions utilizing a Diagnosis Engine. A textual description (e.g., a medical complaint, or any suitable text/description in any suitable domain) can be received and used as input to the Diagnosis Engine. The Diagnosis Engine may utilize discourse analysis to split the complaint into fragments so that each fragment can be associated with an illness description or symptom description. In the case of multiple diseases, discourse analysis may be used to verify coordination between i) the rhetorical relationships between the fragments and ii) extended discourse-like relations between the symptom descriptions, such as "one disease causes another" or "one disease follows another." Matching of texts can be performed by means of joint syntactic and semantic representation alignment based on an abstract graph alignment algorithm. The Diagnosis Engine can utilize discourse-level relationships between cases.

Medical diagnosis is the process of determining the cause of a patient's illness or condition by investigating information acquired from various sources including physical examinations, patient interviews, laboratory tests, the patient's medical records and the patient's family medical record, and existing medical knowledge of the cause of observed signs and symptoms. Obtaining a correct diagnosis is the most crucial step in treating a patient as it assists doctors in finding the best treatment for the patient's condition. However, it is a complicated process requiring a lot of manual efforts that can be time-consuming. Because of the complex nature of this process, it is subject to various errors and misdiagnosis is very common. According to the World Health Organization, each twentieth patient was misdiagnosed in 2015. This is a unsettling, especially when people lives are at stake.

A Diagnosis Engine is disclosed that is configured to receive a textual description of patient medical complaint as input and attempts to find symptom descriptions and/or labeled cases to identify the disease or illness. In some embodiments, the textual description may be split into multiple fragments to diagnose multiple diseases by finding symptom descriptions and/or labeled cases for each fragments such that:

1) If multiple sources are matched with a fragment, a consensus may be enforced to confirm the diagnosis for individual disease
2) When multiple sources are identified for multiple fragments, the relations between these sources may need to agree with the relations between the fragments the textual description is split into.

In some embodiments, the input of Diagnosis Engine can be a medical record. As the original resource for medical management, medical records can provide a good summary of clinical experiences and can be a valuable source for knowledge accumulation. With the rapid development of information technology and its in-depth application in hospitals, electronic medical records are emerging and tend to be increasingly intelligent. Different intelligent methods, such as ontology, semantic analysis, natural language processing, and fuzzy logic can be applied to medical record processing. In an electronic medical record system, a medical record interface, diagnosis-specific visualizations of electronic medical records, and medical record validation are beneficial in many medical fields (e.g., cardiology). The relevant computer-aided systems are also applied in dental fields.

A diagnosis of a disease, illness, or a condition may rely on information which contains factors which make providing an accurate diagnosis difficult. These factors include ambiguity, uncertainty, conflicts, and resource and organizational constraints. A lot of symptoms are nonspecific and variable, and may depend on the person. Many diagnostic tests are expensive, not regularly done, and often do not give a binary answer (e.g., yes/no, true/false, etc.). Physicians can incorrectly apply heuristics during the diagnosis stage and/or can be more biased towards disease or conditions which they have diagnosed in the past. Physicians may trust the initial diagnostic impression, even though the further information might not support that initial assumption. The Diagnosis Engine is intended to mitigate these tendencies.

Medical reasoning involves processes that can be systematically analyzed, as well as those characterized as implicit, and thus, not easily interpretable. In medicine, the experts not only use rules to diagnose a problem, but they also use a mixture of textbook knowledge and experience. The experience consists of cases, typical and exceptional ones, and the physicians take them into account for reasoning.

"Case-Based Reasoning" (CBR) refers to a methodology for reasoning on computers that attempts to imitate the behavior of a human expert and learns from the experience of past cases. Case-Based Reasoning (CBR) methods can be very efficient in the domain of medical diagnosis, at least because reasoning with cases corresponds with the typical decision making process of physicians. Also, incorporating new cases means automatically updating parts of the changeable knowledge. However, CBR is not always successful in the medical domain, as it is in other fields for building intelligent systems. More precise text-based similarity computing is needed.

In some embodiments, the CBR techniques disclosed herein are combined with syntax and semantics for textual matching. In some cases, in order to recognize matching medical records, it may be necessary to establish a match between the different parts of disparate records of various cases, rather than attempting to match a user's query to a single medical record. Thus, in some embodiments, user input (e.g., input comprising a textual medical complaint, a user's medical record(s), a text and/or description, etc.) can be split into fragments to be matched with texts of known, previously-classified documents. For example, discourse analysis can be used to help identify logically connected fragments of the user input. Relationships between these fragments can be established. For each fragment, one or more matching cases can be identified from a corpus that includes textual documents that have been previously labeled with an associated diagnosis label (e.g., indicating an associated disease, illness, and/or condition). A response may be provided to the user. The response may include information associated with the disease, illness, and/or condition and/or information obtained from the one or more matching cases.

A dianosis engine, as discussed herein, can be configured to perform offline and online operations as described below. As part of an offline procedure, the diagnosis engine (e.g., the diagnosis engine described in more detail with respect to FIG. 4) may:

1) Maintain a set of symptom descriptions each associated with a particular diagnosis and/or a set of case data for a plurality of cases, each case being associated (e.g., labeled) with a diagnosis. Collectively, these symptom descriptions and/or case data may be referred to as a known-case library.
2) Use discourse analysis to build discourse trees of each portion (e.g., paragraph, sentence, document) of each of the documents of the known-case library.
3) Identify relationships between portions of different documents based on identifying common entities (e.g., keywords) from each discourse tree.
4) Construct extended discourse trees based at least in part on building rhetorical links identifying the relationships between text fragments in different paragraphs, sentences, and/or documents of different discourse trees.

As part of an online procedure, the diagnosis engine may:

1) Receive input comprising a patient's complaint or health record.
2) Generate a discourse tree from the text of the patient's complaint/health record to split the input into multiple fragments.
3) Match the multiple fragments of the text to one or more fragments of the known-case library based at least in part on performing syntactic generalization between each fragment of the input to fragments of the known-case library. This essentially identifies common words (or synonymous words) between the fragment of the input and a fragment of the known-case library.
4) Identify rhetorical relationships between the fragments of the text.

5) Use the relationships identified in the extended discourse tree associated with each of the known-case fragments to verify that the relationships between the fragments of input agree with the relationships identified in the extended discourse tree of the known-case fragment.
6) If the relationships between fragments of the patient's complaint/health record match the relationships between fragments of known cases, then label the fragment(s) of the patent's complaint/health record with the label associated with the known-case fragment(s).
7) If the relationships between fragment(s) of the patient's complaint/health record do not match the relationships between fragment(s) of known cases, then use the discourse tree to split the text into different fragments and attempt steps 3-7 as many times as necessary to find a match that indicates the relationships between the fragments of the complaint/health record match the relationships between fragments associated with the known cases.

FIG. 1 depicts autonomous agent environment 100, in accordance with at least one embodiment.

FIG. 1 depicts computing device 102, data network 104, and user device 106. The computing device 102 may further include database 110 and training data 112. User device 106 may include user interface 114. Training data 112 may be utilized to train classifier 120 to identify answers from corresponding queries (e.g., natural language queries also referred to as "questions") provided at user interface 114.

User device 106 can be any mobile device such as a mobile phone, smart phone, tablet, laptop, smart watch, and the like. User device 106 communicates via data network 104 to computing device 102. Data network 104 can be any public or private network, wired or wireless network, Wide Area Network, Local Area Network, or the Internet.

The classifier 120 may be previously trained by the computing device 102 and/or any suitable system to identify output data from input data. The classifier 120 may include one or more predictive models, classification models, neural networks, and so on. In some embodiments, classifier 120 may be trained utilizing any suitable supervised learning algorithm in which a function (sometimes referred to as "a model") is trained to identify output (e.g., an answer) from provided input (e.g., a natural language query) based at least in part on a training data set including input/output pairs (e.g., other input data previously paired with corresponding output decisions). The classifier 120 can be utilized in any suitable context to provide any suitable decision from input data. In some embodiments, the autonomous agent application 108 may be configured to train the classifier 120 from training data 112 (e.g., a number of example question (input) and answer (output) pairs), or the autonomous agent application 108 may obtain the (already trained) classifier 120 from memory or another system. In some embodiments, the output (e.g., an answer) provided by the classifier 120 may include a decision log which includes the specific factors (e.g., specific user data) which influenced the decision of which answer to provide. In some embodiments, the output may be stored in database 110 and/or the input utilized by the classifier 120 and the corresponding output provided by the classifier 120 may be stored as additional training data within training data 112.

In an example, the database 110 may include a corpus of documents (e.g., documents corresponding to previously labeled medical cases, each being labeled as being associated with one or more diseases, illnesses, and/or conditions).

The database 110 may further include a set of answers. Each answer may be indexed (e.g., associated) with one or more labels identifying one or more diseases, illnesses, and/or conditions with which the answer is related. A subsequent natural language query may be received at the user device 106 via the user interface 114. The natural language query may be transmitted to the autonomous agent application 102. In some embodiments, the natural language query may include user input (e.g., a question, one or more medical records, etc.) indicating one or more symptoms. A process for classifying the user input utilizing one or more historic cases may be performed. Discourse analysis may be utilized to separate the user input into multiple fragments. Each fragment may be matched to a case from the corpus. If multiple cases are matched with a fragment, a consensus may be enforced to confirm the diagnosis for an individual disease, illness, and/or condition. When multiple cases are identified for multiple fragments of the user input, the relations between these sources may need to agree with the relations between the fragments of the user input. The user input can be associated with a classification (or more than one classification label) that corresponds to the labels associated with the matches cases. In some embodiments, an answer may be selected based at least in part on the classification(s) and provided in response to the user input.

Figure 2:
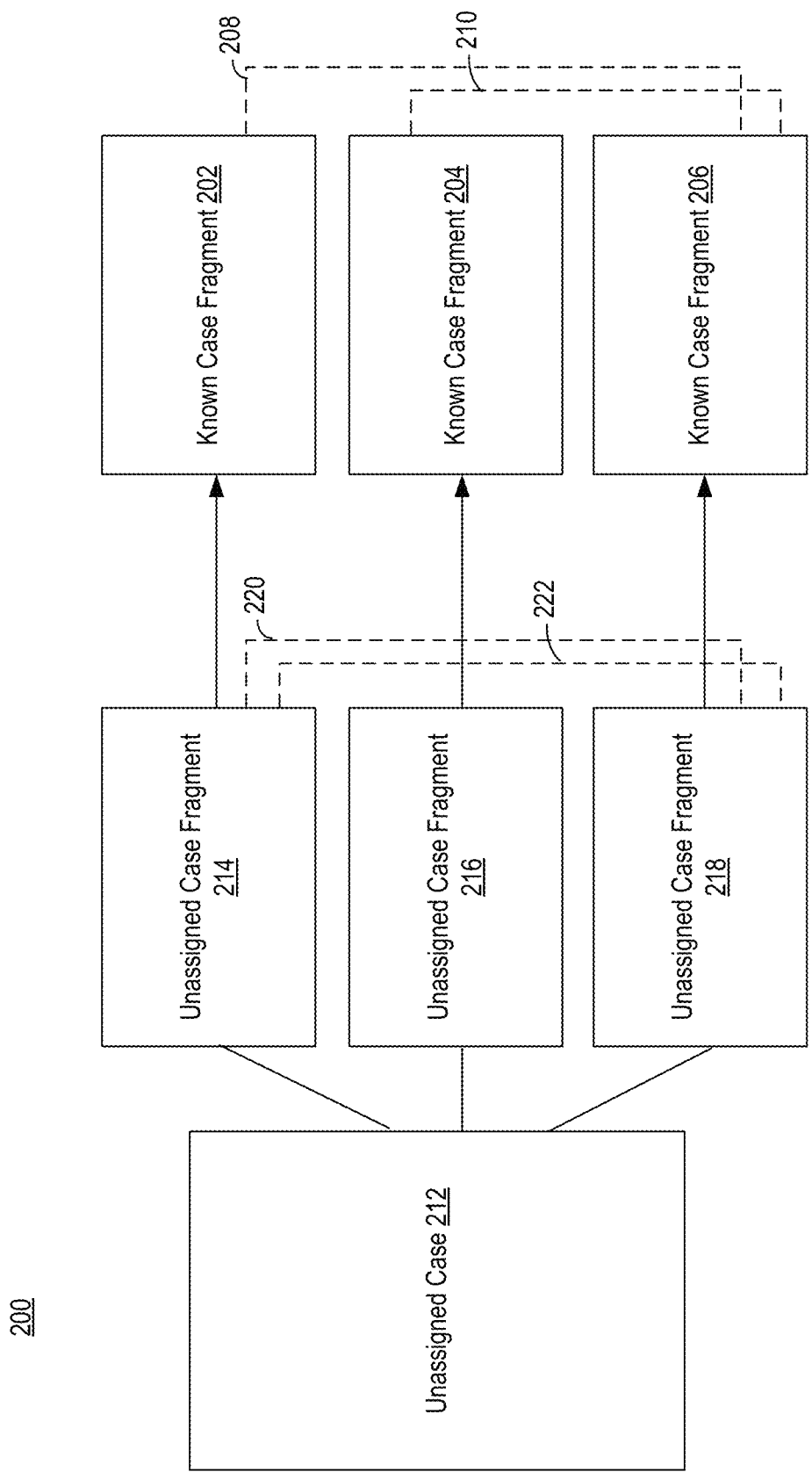
FIG. 2 is a block diagram depicting an example set of components of a system that utilizes multi-case-based reasoning, in accordance with at least one embodiment.

FIG. 2 is a block diagram 200 depicting an example set of components of a system that utilizes multi-case-based reasoning, in accordance with at least one embodiment.

As used herein, "textual unit" refers to a unit of text. Examples include an elementary discourse unit, phrase, fragment, sentence, paragraph, page, and document.

As used herein, "entity" refers to something with a distinct and independent existence. An entity may be used in a textual unit. Examples of entities include a person, a company, a location, a thing, a name of a document, or a date or time.

As used herein, "rhetorical structure theory" is an area of research and study that provided a theoretical basis upon which the coherence of a discourse could be analyzed.

As used herein, "discourse tree" or "DT" refers to a structure that represents the rhetorical relations for a sentence of part of a sentence, paragraphs, and the like. A discourse tree may include any suitable number of nodes in a tree structure. Each nonterminal node represents a rhetorical relationship between at least two fragments and each terminal node of the nodes of the discourse tree is associated with one of the fragments.

As used herein, an "extended discourse tree" refers to a structure that represents multiple discourse trees, where each discourse tree includes a plurality of nodes. Each nonterminal node of a discourse tree represents a rhetorical relationship between at least two fragments of a corresponding document. Each terminal node of the nodes of the discourse tree are associated with one of the fragments. The extended discourse tree indicates one or more rhetorical relationships between the corresponding fragments of the at least two discourse trees. Extended discourse trees includes are used herein to match an unknown case against a structured set of pre-labeled cases. This structure is defined via extended discourse trees. Additional information can be found in U.S. Pat. No. 10,853,574, issued Dec. 1, 2020, entitled "Navigating Electronic Documents using Domain Discourse Trees," the entirety of which is incorporated by reference for all purposes.

As used herein, a "rhetorical relation," "rhetorical relationship," or "coherence relation" or "discourse relation" refers to how two segments of discourse are logically connected to one another. Examples of rhetorical relations include elaboration, contrast, and attribution.

A system can include any suitable number of known cases (e.g., documents associated with known cases that have been indexed and labeled as being associated with a particular disease, illness, and/or condition). In some embodiments, the known cases can be split into fragments (e.g., paragraphs, sentences, phrase, word, document, etc.) by generating various discourse trees that identify rhetorical relationships between these fragments. By way of example, a known case may be split into paragraph fragments 202, 204, and 206 (and/or sentence fragments, and/or word/phrase fragments, etc.) based at least in part on generating a discourse tree of an entire document (e.g., a document including known case fragments 202-206. The generated discourse tree may be utilized to identify various rhetorical relationships (e.g., elaboration, enablement, joint, contrast, temporal, etc.) between these fragments. By way of example, rhetorical relations 208 and 210 may be identified via these one or more discourse trees. Some example rhetorical relations are identified below:

| Relation Name | Nucleus | Satellite |
|---|---|---|
| Antithesis | ideas favored by the author | ideas disfavored by the author |
| Background | text whose understanding is being facilitated | text for facilitating understanding |
| Circumstance | text expressing the events or ideas occurring in the interpretive context | an interpretive context of situation or time |
| Concession | situation affirmed by author | situation which is apparently inconsistent but also affirmed by author |
| Condition | action or situation whose occurrence results from the occurrence of the conditioning situation | conditioning situation |
| Elaboration | basic information | additional information |
| Enablement | an action | information intended to aid the reader in performing an action |
| Evaluation | a situation | an evaluative comment about the situation |

-continued

| Relation Name | Nucleus | Satellite |
|---|---|---|
| Evidence | a claim | information intended to increase the reader's belief in the claim |
| Interpretation | a situation | an interpretation of the situation |
| Justify | text | information supporting the writer's right to express the text |
| Motivation | an action | information intended to increase the reader's desire to perform the action |
| Non-volitional Cause | a situation | another situation which causes that one, but not by anyone's deliberate action |
| Non-volitional Result | a situation | another situation which is caused by that one, but not by anyone's deliberate action |
| Otherwise (anti conditional) | action or situation whose occurrence results from the lack of occurrence of the conditioning situation | conditioning situation |
| Parallel | a situation | a separate situation |
| Purpose | an intended situation | the intent behind the situation |
| Restatement | a situation | a re-expression of the situation |
| Solutionhood | a situation or method supporting full or partial satisfaction of the need | a question, request, problem, or other expressed need |
| Summary | text | a short summary of that text |
| Volitional Cause | a situation | another situation which causes that one, by someone's deliberate action |
| Volitional Result | a situation | another situation which is caused by that one, by someone's deliberate action |

Discourse trees can be generated using different methods. A simple example of a method to construct a DT bottom up is:
(1) Divide the discourse text into units by:
  (a) Unit size may vary, depending on the goals of the analysis
  (b) Typically, units are clauses
(2) Examine each unit, and its neighbors. Is there a relation holding between them?
(3) If yes, then mark that relation.
(4) If not, the unit might be at the boundary of a higher-level relation. Look at relations holding between larger units (spans).
(5) Continue until all the units in the text are accounted for.

Figure 4:
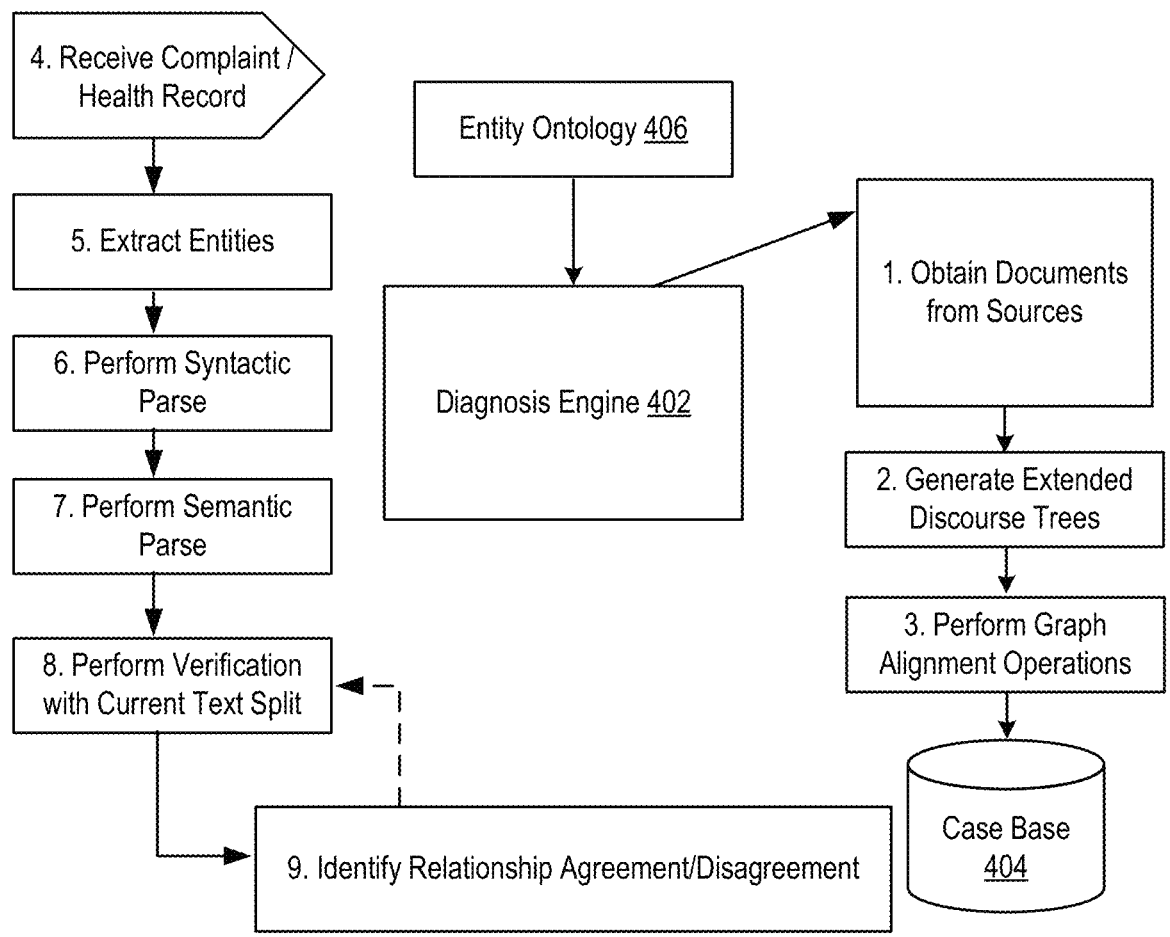
FIG. 4 is a block diagram depicting an example method for classifying unknown cases utilizing a corpus of medical documents, in accordance with at least one embodiment.

In some embodiments that utilize rhetorical structure theory (RST), rhetoric relations are not mapped directly onto texts; they are fitted onto structures called schema applications, and these in turn are fitted to text. Schema applications are derived from simpler structures called schemas (as shown by FIG. 4). Each schema indicates how a particular unit of text is decomposed into other smaller text units. A rhetorical structure tree or discourse tree is a hierarchical system of schema applications. A schema application links a number of consecutive text spans, and creates a complex text span, which can in turn be linked by a higher-level schema application. RST asserts that the structure of every coherent discourse can be described by a single rhetorical structure tree, whose top schema creates a span encompassing the whole discourse.

In some embodiments, an unassigned case 212 may be received. In some embodiments, the unassigned case 212 may include data such as a question/statement (e.g., a question or statement provided via user interface 114 of FIG. 1), documents (e.g., one or more medical records provided via user interface 114), or the like. In some embodiments, the unassigned case 212 may be split into fragments (e.g., unassigned case fragments 214-216) based at least in part on generating a discourse tree from the data of the unassigned case (e.g., a user-provided description of his health, a medical record associated with the user, etc.). By generating this discourse tree, a number of relations (e.g., relations 220 and 222) may be identified. For each unassigned case fragment, a match may be determined (e.g., unassigned case fragment 214 may be matched to known case fragment 202, unassigned case fragment 216 may be matched to known case fragment 204, and unassigned case fragment 218 may be matched to known case fragment 206). In some embodiments, a correspondence between the relations for the unknown case fragments and the relations between the known case fragments are established and approved. For example, relations 220 and 222 may be established and compared to relations 208 and 210. Because the fragments 214-216 correspond/match to known case fragments 202-206, and the relations 220 and 222 are determined to indicate the same types of relations as 208 and 210, respectively, the unassigned case 212 may be identified as being related to the same illness(es) with which known case fragments 202-206 are associated.

A multi-CBR strategy can be formulated as follows:
1) A case to be recognized (seed) is split into subcases for matching;
2) Relations are established between the subcases;
3) For each subcase, a match to a known case is established;
4) Relations between known cases are identified;
5) A correspondence between the relations for the unknown subcases and the relations between the known cases is established and approved;
6) Unknown case is recognized (assigned a class).

As a specific multi-CBR scenario where cases are texts:
Relations between the portions of text are rhetorical relations of discourse analysis
Relations between cases can be case hierarchy or ontology-based that can be mapped into rhetorical relations In some embodiments, the unassigned case 212 includes patient's records with complaints that contain multiple illnesses. The known case fragments may include instructions on illness diagnoses and sample disease descriptions. In terms of search engineering, there is a major difference between a conventional search and multi-CBR search. In the conventional search, its results (documents) are obtained and ranked, and no search constraints are associated with relationships or links between ranked search results. Conversely, under multi-CBR, search results come as a structured set of documents with certain relations between them.

Consider the following description of a patient problem:

---

I experience fatigue and hunger, because I do not acquire enough energy from the meals I eat. I urinate and feel thirsty fairly frequently. I lack a sharpness of vision resulting in the inability to see fine detail.
Later I started feel tingling in the hands and feet. After that, I feel numbness, pain and burning sensations starting in the toes and fingers then continuing up the legs or arms. I lost loss of muscle tone in my hands and feet, as well as a loss of balance.
As a result, I started feeling fatigue, pale skin, chest pain and an irregular heartbeat. I noticed blood in may urine, which is now dark, a drop in mental alertness and itchy skin.

---

FIG. 3 is a block diagram depicting an example discourse tree 300 generated from user input (e.g., the patient problem provided above in connection with FIG. 2), in accordance with at least one embodiment.

The discourse tree 300 with the indentation denoting the level of hierarchy is shown in FIG. 3. To find a split, a higher-level rhetorical relations (here, Elaboration) is selected such that in each fragment there is a non-default rhetorical relation of Explanation, Enablement, Cause or another one. Using these rhetorical relations, text fragments 302, 304, and 306 are identified. An example is now given utilizing syntactic similarity assessment implemented to identify a mapping between corresponding (synonymous) entities and phrases.

Known Case Fragment (associated with Diabetes): Symptoms of diabetes included increased thirst, frequent urination, extreme hunger and unexplained weight loss. There is a presence of ketones in the urine, a drop in mental alertness and itchy skin.

Fragment 302: I experience fatigue and hunger, because I do not acquire enough energy from the meals I eat. I urinate and feel thirsty fairly frequently. I lack a sharpness of vision resulting in the inability to see fine detail.

The fragments may be generalized using any suitable syntactic generalization technique and expressed in a simple first-order representation. For example, the known case fragment above may be generalized to: urination(frequent), hunger(high), thirst(frequent). Rhetorical relations between fragments 302-306 are extracted and generalized. For example, fragment 302 may also be generalized to: urination (frequent), hunger(high), thirst(frequent). Thus, fragment 302 may be matched to the known case fragment provided above through generalization and matching rhetorical relations.

In some embodiments, a complaint (e.g., an unassigned case) may include mixed descriptions of symptoms (e.g., symptoms for two illnesses). However, when a patient describes her complaints in plain words, we would expect a smoother text that can be naturally subject to discourse processing. A patient would likely formulate a complaint to cause compassion and reflect her perception of the illness, express her expectation for treatment and recovery. Therefore, a patient complaint can be rich with discourse markers. In some embodiments, a parallel relation may be used to infer that the patient is expressing two (or more) sets of symptoms at the same time such that the text can be split according to these two (or more) sets. Each of these parallel sets of symptoms can be similarly mapped to known case fragments and the rhetorical relations between such fragments may be identified and verified.

FIG. 4 is a block diagram depicting an example method 400 for classifying unknown cases utilizing a corpus of medical documents (e.g., previous cases for which diagnosis are known (referred to as "known cases") and/or disease/illness/condition descriptions), in accordance with at least one embodiment.

At step 1, various documents (e.g., case data including medical records previously associated with one or more diseases/illnesses/conditions, a set of symptom descriptions each associated with a particular diagnosis, etc.) are obtained. Collectively, these symptom descriptions and/or case data may be referred to as a "known-case library."

At step 2, a number of extended discourse trees may be generated.

Figure 5:
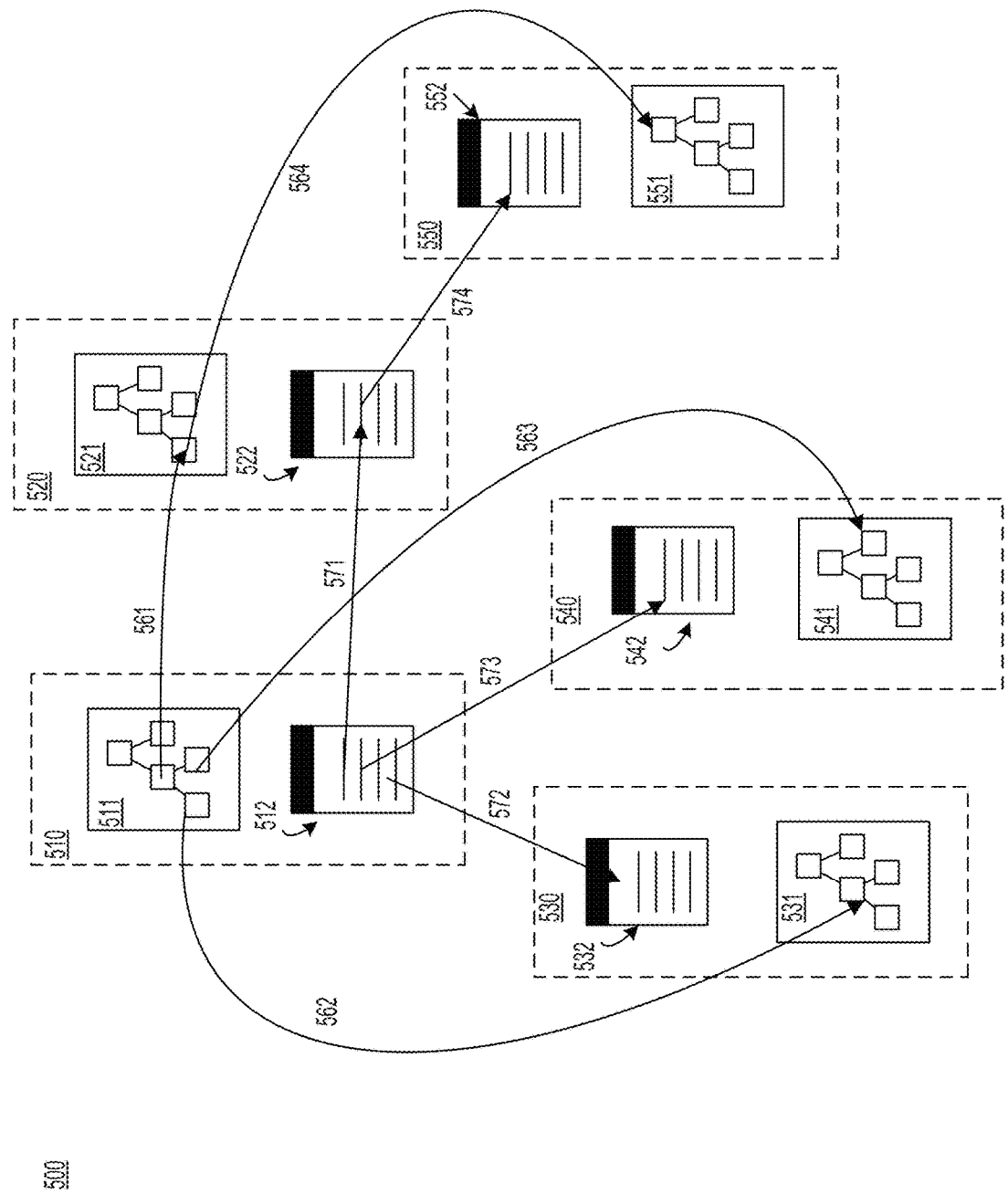
FIG. 5 is a block diagram depicting an example extended discourse tree (EDT), in accordance with at least one embodiment.

FIG. 5 is a block diagram depicting an example extended discourse tree (EDT) 500, in accordance with at least one embodiment.

Aspects of the present disclosure facilitate navigating an extended discourse tree built from a corpus of relevant content such as multiple documents (e.g., multiple medical records, disease descriptions, etc.). An extended discourse tree (e.g., EDT 500) is a combination of discourse trees (DTs) of individual textual units (e.g., paragraphs, sentences, phrases, etc.) from multiple documents. Aspects use extended discourse trees to not only allow zooming in based on keywords but also on navigating in or out or back based on how documents are interconnected, thereby enabling an autonomous agent to provide content navigation such as guided search.

Extended discourse tree 500 includes groups 510, 520, 530, 540, and 550. Each group includes a document and a discourse tree (DT) generated from the document. For example, group 510 includes discourse tree 511 and document 512, group 520 includes discourse tree 521 and document 522, and so on.

In addition to links between within particular discourse trees, e.g., discourse trees 511, 521, 531, 541, and 551, extended discourse tree 500 includes inter-discourse tree links 561-564 and associated inter-document links 571-574. The diagnosis engine 402 of FIG. 4 may construct discourse trees 511-515. Discourse tree 511 represents document 512, discourse tree 521 represents document 522, and so on. Extended discourse tree 500 can be built by building a discourse tree for each paragraph, sentence, phrase, document, and the like.

Inter-discourse tree link 561 connects discourse tree 511 and 521, inter-discourse tree link 562 connects discourse tree 521 and 531, inter-discourse tree link 563 connects discourse tree 511 and 541, and inter-discourse tree link 564 connects discourse tree 521 and 551. Based on inter-discourse tree links 561-564, diagnosis engine 402 creates inter-document links 571, 572, 573, and 574, which correspond to inter-discourse tree links 561, 562, 563, and 564 respectively. Inter-document links 571-574 can be used to navigate documents 512, 522, 532, 542, and 552.

Diagnosis engine 402 can determine one or more entities within a first discourse tree of the discourse trees 511-515. Examples of entities include places, things, people, or companies. Diagnosis engine 402 can then identify the same entities present in the other discourse trees. Based on the determined entities, diagnosis engine 402 can determine a rhetorical relationship between each matching entity.

For example, if an entity "San Francisco" occurs in document 512, e.g., "San Francisco is in California," and document 522 further explains that "San Francisco has a moderate climate but can be quite windy," diagnosis engine 402 would determine that the rhetorical relationship between the entity "San Francisco" is one of elaboration and mark links 561 and 571 as elaboration. Continuing the example, diagnosis engine 402 determines links 562-564 and corresponding links 572-574 based on determined rhetorical relations. Diagnosis engine 402 can combine the discourse trees of the paragraphs of the documents to form extended discourse tree 500.

By using the links in extended discourse tree 500, diagnosis engine 402 can navigate between paragraphs of the same document or between documents, e.g., document 512 and 522. For example, if a user is interested in more information on a particular topic, diagnosis engine 402 can navigate through an elaboration rhetorical relation from nucleus to satellite within a paragraph or an elaboration rhetorical relation hyperlink to a document that offers more specific information on the topic.

Conversely, if a user decides that a suggested topic is not exactly what is needed, the user can return to a higher-level view of the documents (e.g., from satellite to nucleus, or from narrow document to broad document). In turn, diagnosis engine 402 navigates an elaboration relationship in the opposite order, i.e., from a satellite to the nucleus at either the paragraph or between documents. Similarly, diagnosis engine 402 facilitates other navigation options such as relying on contrast or condition rhetorical relationships for exploring controversial topics.

To build rhetoric links between text fragments in different paragraphs, sentences, phrases, words, or documents, diagnosis engine 402 identifies a relationship between entities by using a fictitious text fragment, or a temporary paragraph/sentence/phrase/word/document, from the respective text fragments of the original paragraph and perform co-reference analysis and discourse parsing on the paragraph.

In some embodiments, a set of medical documents can be obtained (input) and an extended discourse tree (e.g., extended discourse tree 500) may be generated (as output). The EDT may be encoded as a regular discourse tree with the labels of document identification for each node. For example purposes, the example below is described with respect to two documents, any number of documents may be utilized.

A first document and a second document may be accessed. Examples of documents include texts, books, news articles, medical journals, disease/illness/condition descriptions, medical records, physician notes, and other electronic documents. The diagnosis engine 402 may identify similarities in keywords between documents by scoring the content of each document. For example, diagnosis engine 402 determines that a first content score for the first document and a second content score for the second document are within a threshold and based on the similarity, uses the first and second documents to create an extended discourse tree.

In an aspect, diagnosis engine 402 performs document analysis that includes the generation of document trees representing the sentential and phrasal structure of the document. Rhetorical relations associated with an inter-document link can determine different navigation scenarios. By default, elaboration can be used. Diagnosis engine 402 offer a link to another document that is related by an attribution relation if the user is interested in questions such as "why," or "how." Diagnosis engine 402 can offer a link to a document that is related by a contrast relation if a user expresses disagreement with an originally presented document or asks for a document that provides a counterpoint to the current document.

In a further aspect, diagnosis engine 402 obtains the first and second document by executing a user query. Examples of user queries include "diabetes" or "documents on Crohn's disease."

Diagnosis engine 402 can first create a first discourse tree for a first paragraph of a first document. Diagnosis engine 402 accesses a paragraph from the first document. Each sentence of the paragraph includes fragments, or elementary discourse units. At least one fragment includes a verb. Each word in the fragment includes role, e.g., the function, of the word within the fragment. Diagnosis engine 402 can generate a discourse tree that represents rhetorical relationships between the fragments. The discourse tree includes multiple nodes, each nonterminal node representing a rhetorical relationship between two fragments and each terminal node associated with one of the fragments. Diagnosis engine 402 continues in this manner, building a set of discourse trees for each paragraph in the first document. Although this process is described with respect to a paragraph as a unit of text, other sizes of text can be used (e.g., sentences, phrases, words, etc.).

Diagnosis engine 402 creates second discourse tree for a second paragraph of a second document. Diagnosis engine 402 performs substantially similar steps for the second document as performed for the first document. In the case that diagnosis engine 402 creates an extended discourse tree for more than two documents, similar operations may be performed on each document to generate a corresponding discourse tree. Diagnosis engine 402 can iterate through all pairs of discourse trees (i and j) in the set of discourse trees where each discourse tree corresponds to a document. Pairs of discourse trees can be represented by:

$DT_i$ and $DT_j \in DT_a$.

Diagnosis engine 402 may determine an entity and a corresponding first elementary discourse unit from the first discourse tree. Various methods can be used such as keyword processing (searching for one of a list of predefined keywords in the sentences of the first document), using a trained machine-learning model, or searching an internet resource. Diagnosis engine 402 identifies all noun phrases and named entities in the discourse trees $DT_i$ and $DT_j$.

In some embodiments, diagnosis engine 402 extracts a noun phrase from the discourse tree. Diagnosis engine 402 can then classify the noun phrase as either (i) an entity or (ii) not an entity by using a trained machine learning model.

Diagnosis engine 402 determines, in the second discourse tree, a second elementary discourse unit that matches the first elementary discourse unit. More specifically, diagnosis engine 402 computes overlap and identify common entities $E_{i,j}$ between $DT_i$ and $DT_j$. Diagnosis engine 402 establishes relationships between occurrences of entities in $E_{i,j}$ such as equals, sub-entity, or part-of Diagnosis engine 402 then forms inter-paragraph rhetorical links $R(E_{i,j})$ for each entity pair occurrence in $E_{i,j}$.

Responsive to determining a rhetorical relationship between the first elementary discourse unit and the second elementary discourse unit, diagnosis engine 402 links the first discourse tree and the second discourse tree via the rhetorical relationship, thereby creating an extended discourse tree. More specifically, diagnosis engine 402 classifies a rhetorical relation for each rhetorical link by forming a merging of text fragments, e.g., $EDU(E_i)$ and $EDU(E_j)$, building its DT and using recognized relation label for this rhetorical link.

In an aspect, diagnosis engine 402 combines the first elementary discourse unit and the second elementary discourse unit into a temporary paragraph. Diagnosis engine 402 then determines a rhetorical relationship between the first and second elementary discourse units within the temporary paragraph by applying discourse parsing to the temporary paragraph.

In a further aspect, responsive to not determining a rhetorical relationship, diagnosis engine 402 creates a default rhetorical relationship of type elaboration between the first elementary discourse unit and the second elementary discourse unit and links the first discourse tree and the second discourse tree.

In an aspect, diagnosis engine 402 performs automated building and categorizing of links between textual spans across documents. Here the following family of approaches can be used: lexical distance, lexical chains, information extraction, and linguistic template matching. Lexical distance can use a cosine similarity across pairs of sentences, and lexical chains can be more robust leveraging synonymy and hypernymy.

Extended discourse trees can form relationships between two or more documents at different levels of granularity. For example, relationships can be determined between elementary discourse units, as described with respect to process 1200. Additionally, extended discourse trees can represent relationships between words, sentences, paragraphs, sections of documents, or entire documents. As depicted, each individual graph consists of smaller subgraphs for each individual document. Links are shown that represent logical connection between topics within a single document.

Figure 6:
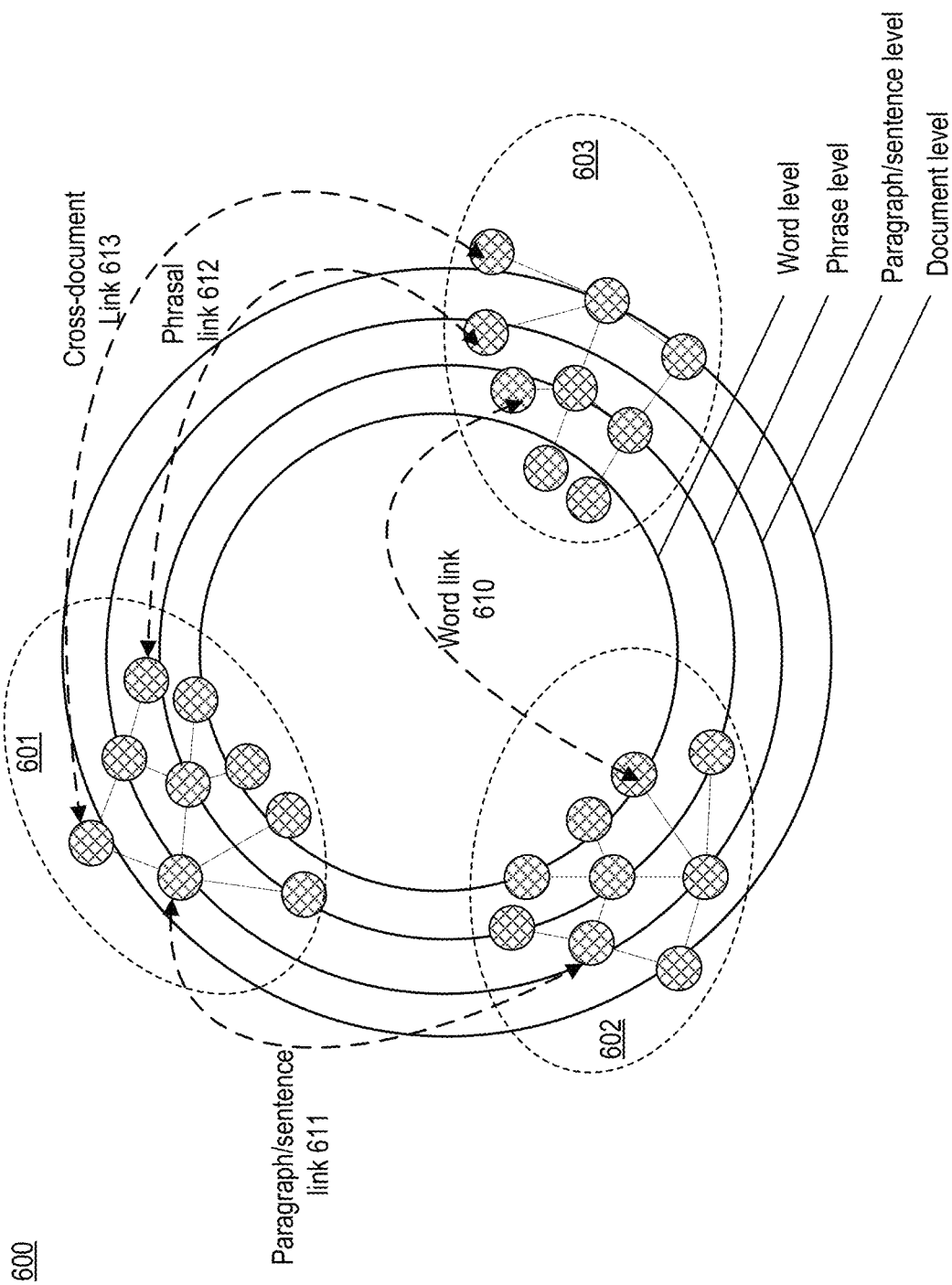
FIG. 6 depicts a navigation graph that illustrates relationships between textual units of documents at different levels of granularity, in accordance with at least one embodiment.

FIG. 6 depicts a navigation graph 600 that illustrates relationships between textual units of documents at different levels of granularity, in accordance with at least one embodiment.

FIG. 6 depicts discourse trees 601, 602, and 603, each corresponding to a separate document. FIG. 6 also depicts various inter-document links, such as word link 610 that links words in documents 602 and 603, paragraph/sentence link 611 that links paragraphs or sentences in documents 601 and 602, phrasal link 612 that links phrases in documents 601 and 603, and cross-document link 613 that links documents 601 and 603. Diagnosis engine 402 can use links 610-613 to navigate between documents 601-603.

In some embodiments, the navigation graph 600 may be generated based at least in part on executing a clustering algorithm to group documents based on document similarity. Another option is to identify clusters as being the sets of documents returned by a search engine: the results will depend on a user query. By way of example, a search query such as "Diabetes" can return a set of documents that are indexed with the term "diabetes." These search results can be considered a cluster.

The second step may include the generation of discourse trees representing the sentential and phrasal structure of the document. The third step is an automated building and categorizing of links between textual spans across documents. Here, at least one of the following approaches can be used: lexical distance, lexical chains, information extraction, linguistic template matching, and the like. Lexical distance can use a cosine similarity across pairs of sentences, and lexical chains can be more robust leveraging synonymy and hypernymy.

A graph-based operator defines a transformation on a multi-document navigation graph (MDNG) G (also referred to herein as a "navigation graph") that preserves some of its properties while reducing the number of nodes. An example of such an operator is the link-preserving graph cover operator. Its effect is to preserve only these nodes from the source MDNG that are associated with preferred cross-document links. In this example, the central circled area represents the summary subgraph $G_1$ of G that contains all five cross-document links and only these nodes and edges of G which are necessary to preserve the textual structure of $G_1$.

The navigation graph 600 represents text simultaneously at different levels of granularity (words, phrases, sentences, paragraphs and documents). The navigation graph 600 includes smaller subgraphs for each individual document, which in turn include discourse trees. Two types of links are employed: The first type represents inheritance relationships among elements within a single document. The second type represents semantic relationships among textual units. The example illustrates sample links among documents, phrases, sentences, and phrases.

The processing flow for generating the navigational graph 600 may include:

1) Building a set of all DTs for each paragraph in each document DTA;
2) Iterate through all pairs of $DT_i$ and $DT_j \in DTA$;
3) Identify noun phrases and named entities in $DT_i$ and $DT_j$;
4) Compute overlap and identify common entities $E_{ij}$ between $DT_i$ and $DT_j$;
5) Establish relationships between occurrences of entities in $E_{ij}$ such as equals, sub-entity, part-of;
6) Confirm these relationships by forming text fragment merging $EDU(E_i)$ and $EDU(E_j)$ and applying coreference resolution;
7) Form an inter-paragraph rhetorical links $R(E_{ij})$ for each entity pair occurrence in $E_{ij}$;
8) Classify rhetorical relation for each rhetorical link by forming a text fragment merging $EDU(E_i)$ and $EDU(E_j)$, building its DT and using recognized relation label for this rhetorical link.

Returning to the example of FIG. 4. At step 3, graph alignment operations may be performed (e.g., to classify documents with the labels of already classified documents). Linguistic similarity can be computed as maximal common subtree of syntactic parse trees (e.g., discourse tree). The maximal common subtree can be identified (at least initially) via phrase-level alignment. To thoroughly track the phrase structure at various linguistic levels (phrase, sentence, paragraph), a full-scale graph alignment approach may be applied to avoid losing potentially important linguistic features. These features might play a role in finding correspondence between how patient describe their symptoms and how they are described by physicians in symptom checking instructions.

A graph alignment algorithm may be used for multiple text alignment under case-based reasoning (CBR). The purpose of alignment is two-fold:
1) combine structural information about a text (such as a question) and
2) assess its similarity of meaning to another text, such as an answer.

Syntactic, semantic or joined graph alignment problem can be formulated as follows. We denote the two graphs that we are aligning by $G_1=(V_1, E_1)$ and $G_2=(V_2, E_2)$, where $V_i$ is the set of nodes and $E_i$ is the set of edges in graph $G_i$. We assume that $|V_1| \leq |V_2|$. An injective mapping (that does not map two nodes into one) may be built to align each node in $G_1$ to exactly one node in $G_2$ with a similar topological neighborhood (syntactic and/or semantic properties). Formally, topological similarity of nodes is defined by using the notion of 73-dimensional "graphlet degree signatures" and the "signature similarity" measure specified below. This approach produces a global network alignment, since our node mapping is defined for all nodes in $V_{G1}$. Thus, we do not allow "gaps", i.e., nodes without a match, in $G_1$, but we do allow them in the larger network, $G_2$.

A query graph can be defined that can be mapped to a logical form in λ-calculus and is semantically closely related to λ-dependency-based compositional (DCS)semantics. For expression 'citizens who live in Boston" the regular λ-calculus gives λx.∃e.PlacesLive(x, e) ∧Location(e, Boston) and λ-DCS gives PlacesLive.Location.Boston. Hence, DCS attempts to remove explicit use of variables; it makes it similar in flavor to dependency-based compositional semantics.

Matching semantic parse for Q against that of for A is formulated as query graph generation in the form of a state transitions from a seed alignment towards a full alignment. Each state is a candidate mapping between parses such as abstract meaning representation (AMR)AMR(Q)→AMR (A) in the query graph representation and each action defines a way to grow the alignment. An abstract meaning representation (AMR) are rooted, labeled graphs that abstract away from syntactic idiosyncrasies. The same AMR graph can be assigned to sentences that have the same basic meaning. For example, "he described the banana as yellow," would be assigned the same AMR as "the banana was yellow, according to his description." The representation power of the alignment of a pair of semantic parses is controlled by the set of allowed alignment actions applicable to each state. In particular, the actions are split into three main steps: locating the topic entity in the question, finding the main relationship between the answer and the topic entity, and expanding the query graph with additional constraints that describe properties the answer needs to have, or relationships between the answer and other entities in the question.

When aligning an AMR(V,E) against syntactic dependency parse tree T(U,F) or another AMR graph, the costs of aligning each node v in AMR with each node n in T may be computed. The cost of aligning two nodes can take into account the graphlet degree signature similarity between them, modified to reduce the cost as the degrees of both nodes increase, since higher degree nodes with similar signatures provide a tighter constraint than correspondingly similar low degree nodes. In this way, the densest parts of the AMR graph may be aligned first.

Graphlets can be defined as small connected non-isomorphic induced subgraphs of a large graph such as AMR graph. We now introduce graphlet degree vectors (signatures) and signature similarities to support graph alignment procedure. This measure generalizes the degree of a node, which counts the number of edges that the node touches, into the vector of graphlet degrees, or graphlet degree signature, counting the number of graphlets that the node touches at a particular orbit, for all graphlets on 2 to 5 nodes.

Graphlets are small connected non-isomorphic induced subgraphs of a large network. An induced subgraph must contain all edges between its nodes that are present in the large network, while a partial subgraph may contain only some of these edges. Moreover, graphlets do not need to be over-represented in the data when compared with randomized networks. Graphlets can be used as a basis for designing three highly sensitive measures of network local structural similarities: the relative graphlet frequency distance, the graphlet degree distribution agreement and a network topological similarity measure that generalizes the degree of a node in the network to its graphlet degree vector or graphlet degree signature.

The resulting vector of seventy-three coordinates is the signature of a node that describes the topology of node's neighborhood and captures its interconnectivities out to a distance of 4. The graphlet degree signature of a node provides a highly constraining measure of local topology in its vicinity and comparing the signatures of two nodes provides a highly constraining measure of local topological similarity between them.

The signature (graphlet) similarity is computed as follows. For a node u in graph G, $u_i$ denotes the $i^{th}$ coordinate of its signature vector, i.e., $u_i$ is the number of times node u is touched by an orbit i in G. The distance $D_i(u,v)$ between the $i^{th}$ orbits of nodes u and v is defined as:

$$D_i(u, v) = w_i \times \frac{|\log(u_i + 1) - \log(v_i + 1)|}{\log(\max\{u_i, v_i\} + 2)},$$

where $w_i$ is the weight of orbit i that accounts for dependencies between orbits. The total distance D(u,v) between nodes u and v is defined as:

$$D(u, v) = \frac{\sum_{i=0}^{72} D_i}{\sum_{i=0}^{72} w_i}.$$

The distance D(u,v) is in [0, 1), where distance 0 means that signatures of nodes u and v are identical. Finally, the signature similarity, S(u,v), between nodes u and v is:

$$S(u,v)=1-D(u,v)$$

Clearly, a higher signature similarity between two nodes corresponds to a higher topological similarity between their extended neighborhoods up to the distance of four. Number four corresponds to a typical maximum number of arguments of a verb node of an AMR graph.

Let deg(v) be the degree of a node v in AMR, let $max_{deg(AMR)}$ be the maximum degree of nodes in AMR, and let S(v, u) be the graphlet degree signature similarity of nodes v and u, and let α be a parameter in [0, 1] that controls the contribution of the node signature similarity to the cost function (that is, 1−α is the parameter that controls the contribution of node degrees to the cost function), then the cost of aligning nodes v and u is computed as:

$$C(v, u) = 2 - \left( (1-\alpha) \times \frac{deg(v) + deg(u)}{\max\_deg(G) + \max\_deg(H)} + \alpha \times S(v, u) \right).$$

A cost of 0 corresponds to a pair of topologically identical nodes v and u, while a cost close to 2 corresponds to a pair of topologically different nodes.

The graph alignment algorithm chooses (as the initial seed) a pair of nodes v and u from AMR and T which have the smallest cost. Ties are broken randomly. Once the seed is found, the spheres of all possible radii around nodes v and u are built. A sphere of radius r around node v is the set of nodes $S_{AMR}(v, r) = \{x \in AMR: d(v, x) = r\}$ that are at distance r from v, where the distance d(v, x) is the length of the shortest path from v to x. Spheres of the same radius in two networks are then greedily aligned together by searching for the pairs $(v', u'): v' \in S_{AMR}(v, r)$ and $u' \in S_T(u, r)$ that are not already aligned and that can be aligned with the minimal cost.

When all spheres around the initial seed (v, u) have been aligned, other nodes in both AMR and T are still unaligned. We repeat the same algorithm on a pair of graphs ($AMR^p$, $T^p$) for p=1 . . . 3 and attempt to identify anew seed again, if necessary. The graph $AMR^p$ is defined as a new graph $AMR^p = (V, E^p)$ having the same set of nodes as AMR and having $(v, x) \in E^p$ if and only if the distance between nodes v and x in AMR is less than or equal to p. In other words $d_{AMR}(v, x) \leq p$.$AMR^1 = AMR$. Using $AMR^p$ (p>1) lets us align a path of length p in one graph to a single edge in another graph, which is analogous to allowing "insertions" or "deletions" in a sequence alignment. The alignment procedure may be stopped when each node from AMR is aligned to exactly one node in T.

The described graph alignment algorithm is used to evaluate the fit of various network models to real-world networks and to discover a new, well-fitting, geometric random graph model for protein-protein interaction networks. A random geometric graph is an undirected graph constructed by randomly placing N nodes in some metric space (according to a specified probability distribution) and connecting two nodes by a link if and only if their distance is in a given range, e.g. smaller than a certain neighborhood radius, r.

Such feature of AMR parsing as abstraction is associated between alignment between words and their semantic representations (not a graph alignment). This feature is closely related to how we extract concepts from AMR and build mappings between word's surface form and its semantic meaning. A graph-based aligner designed specifically for word-to-concept scenario may be used to show that better alignment result could improve the AMR parsing result. Building the alignment between word and AMR concept can be conducted as a preprocessing step. As a result, accurate concept identification crucially depends on the word-to-AMR-concept alignment. Since there is no manual alignment in AMR annotation, either a rule-based or unsupervised aligner may be applied to the training data to extract the mapping between words and concepts. This mapping can then be used as reference data to train concept identification models. The greedily aligns a span of words to graph fragment using a set of heuristic rules. While it can incorporate information from additional linguistic sources such as WordNet, it is not adaptable to other domains. Unsupervised aligners borrow techniques from Machine Translation and treat sentence-to-AMR alignment as a word alignment problem between a source sentence and its linearized AMR graph. A Hidden Markov Model (HMM)-based sentence-to-AMR alignment method may be used with a graph distance distortion model to leverage of the structural information in AMR.

The extended discourse trees generated at step 2 may be stored in case base 404 for subsequent use. Steps 1-3 may be performed as part of pre-processing operations. Diagnosis Engine 402 may be configured to access entity ontology 406, a predefined ontology that includes formal specifications of various entities in the medical domain and relations among them. The entity ontology 406 may be utilized to identify synonymous words and/or phrases corresponding to subsequent requests (e.g., diagnosis requests).

Extended discourse trees such as those created by the process described in connection with FIGS. 5 and 6 can be used to identify potential diagnosis for subsequent diagnosis requests. Extended discourse trees enable different applications such as autonomous agents, improved search and navigation, and question-answer coordination.

By way of example, at step 4, a diagnosis request may be received. In some embodiments, the diagnosis request may include a complaint (e.g., a user provided description that includes at least one symptom). In some embodiments, the diagnosis request may include one or more medical documents (e.g., one or more medical records) in lieu of, or in addition to, the complaint.

At step 5, the complaint and/or medical documents may be analyzed to identify one or more entities. The diagnosis engine 402 may be configured to identify these entities with the entity ontology 406 in order to identify one or more synonymous terms.

At step 6, a syntactic parse may be performed on the complaint and/or medical document(s). By way of example, a discourse tree may be generated in the manner described above in connection with FIG. 5. The discourse tree may represent the sentential and phrasal structure of the complaint and/or medical document(s).

At step 7, operations of a semantic parse may be performed on the complaint and/or medical document(s). Combining knowledge from both term frequency-inverse document frequency (TF*IDF) and word embeddings may be beneficial. Relying purely on the words with the highest IDF component of all words improves the overall similarity assessment quality. Low-IDF words have no clear-cut semantic meaning in a domain such as health, and since these words are present in many sentences, there is more coincidental overlap between non-related sentences. Removing these words from a text representation thus succeeds in pulling apart the average similarity between pairs and between non-pairs.

A learning procedure is now described. For every couple c in the training set we sort the words in both texts ($c^1$) and ($c^2$) according to their document frequency i.e. the word with the lowest document frequency comes first—arriving at ($c^{1'}$) and ($c^{2'}$). Next we multiply the word embedding vector of each word $w_j^{1'}$ and $w_j^{2'}$ with an importance factor $i_j$; these importance factors are global weights that will be learned. Finally, we take the mean of these weighed embeddings to obtain a fixed-length vector $o^1$ for ($c^1$) and $o^1$ for ($c^1$):

$$\forall \ell \in \{1, 2\}: o^\ell = \frac{1}{n_c} \sum_{j=1}^{n_c} i_j \cdot w_j^{\ell'}.$$

First the words in the sentence are sorted according to their IDF-component; next, their 400-dimensional word embedding vectors are multiplied by importance factors, and finally the mean is taken. To learn the importance factors, a loss function may be defined as a function of any couple c that minimizes the distance between the vectors of a pair, and maximizes the distance between the vectors of a non-pair. with d(·) a distance function of choice. A squared Euclidean distance function is used.

$$f(c) \triangleq \begin{cases} d(o^1, o^2) & \text{if } c \text{ is a pair} \\ -d(o^1, o^2) & \text{if } c \text{ is a non-pair} \end{cases}$$

Then the following objective is optimize as a function of the importance factors. A stochastic gradient descent with batches of 100 couples is used.

$$J(i_1, \ldots, i_{n_c}) = \frac{1}{|\mathcal{D}|} \sum_{c \in \mathcal{D}} f(c) + \lambda \sum_{j=1}^{n_c} i_j^2.$$

The importance factors steadily decrease in magnitude; words with a low document frequency therefore weigh much more than words with a high document frequency. The factors at the end are very close to zero.

At step 8, for the current split, the rhetorical relations between text fragments may be analyzed to identify whether the rhetorical relations of the current split match the rhetorical relations identified in any of the fragments of the case base 404.

At step 9, relationship agreement/disagreement may be identified. If a set of relationships between labeled cases is established, it is assessed in terms of agreement with the relations between fragments of the current split. If this agreement is approved (e.g., the relations match), the recognition terminates, the new case may be labeled with the label(s) associated with the approved matched cases, and the approved matched cases form the output. Otherwise, a new spit into fragments is produced once again at step 8 and step 9 may be repeated.

Figure 7:
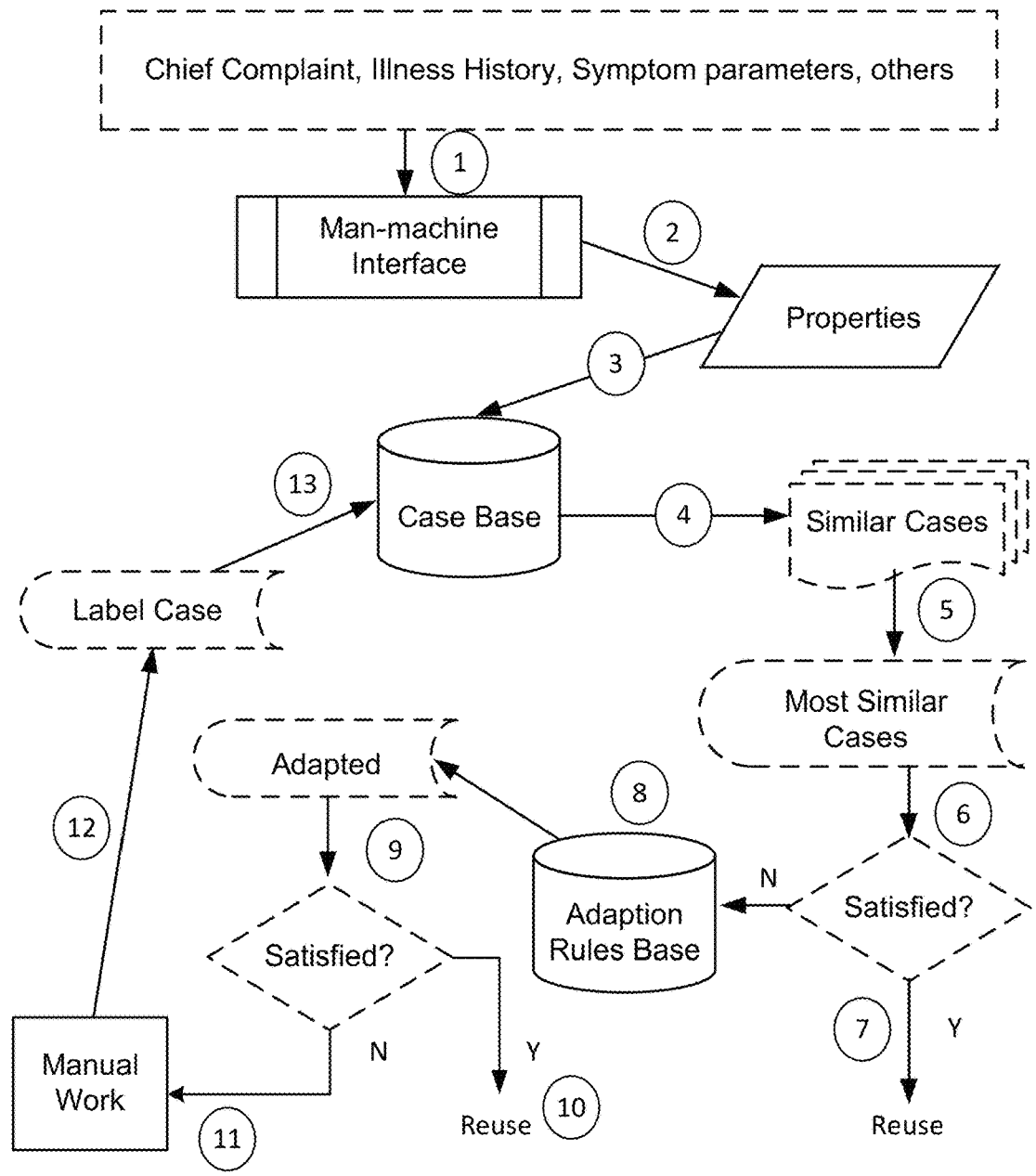
FIG. 7 is a block diagram depicting an example case-based reasoning process, in accordance with at least one embodiment.

FIG. 7 is a block diagram depicting an example case-based reasoning process 700, in accordance with at least one embodiment.

At step 1, a chief complaint, illness history, symptom parameters, or the like may be provided as input to a man-machine interface. The input provided at step 1 may correspond to a new case history.

At step 2, any suitable operations may be performed to extract various properties from the input. By way of example, the input may be parsed into one or more discourse trees that may identify one or more elementary discourse units.

At step 3, the extracted properties may be utilized as search query terms to search a knowledge base (e.g., case base, an example of the case base 404 of FIG. 4).

At step 4, a number of similar cases may be identified and returned based on the search query provided at step 3. By way of example, a nearest neighbor algorithm may be utilized to identify similar cases based at least in part on the properties obtained at step 3.

At step 5, the similar cases may be sorted (potentially) and/or scored based at least in part on a degree to which they are individually similar to the search query terms. In some embodiments, a number of most-similar cases may be selected based at least in part on a predefined rule set.

At step 6, a number of similar cases may be identified and returned based on the search query provided at step 3.

At step 7, if the number of most similar cases meets a predefined threshold (e.g., at least one similar case), and the most similar cases can be used to solve the current case, then reused the most similar cases to provide output indicating a solution to the current case (e.g., instructions for treating the disease/illness/condition with which the user is now diagnosed). If there are not enough similar cases and/or the similar cases cannot be used to solve the current case, then the process may proceed to step 8.

At step 8, the similar case can be adapted according to one or more predefined adaption rules.

At step 9, the adapted case(s) can be analyzed to identify whether they can be utilized to solve the current case. If so, output indicating a solution to the current case can be provided at step 10. Otherwise, the process may proceed to step 11.

At step 11, a further revision of the most similar case may be made with the help of other cases in the knowledge base until a set of requirements are met.

At step 12, the revised case may be labeled with one or more corresponding diseases, illnesses, and/or conditions.

At step 13, the revised case may be stored back in the case base for subsequent use.

Figure 8:
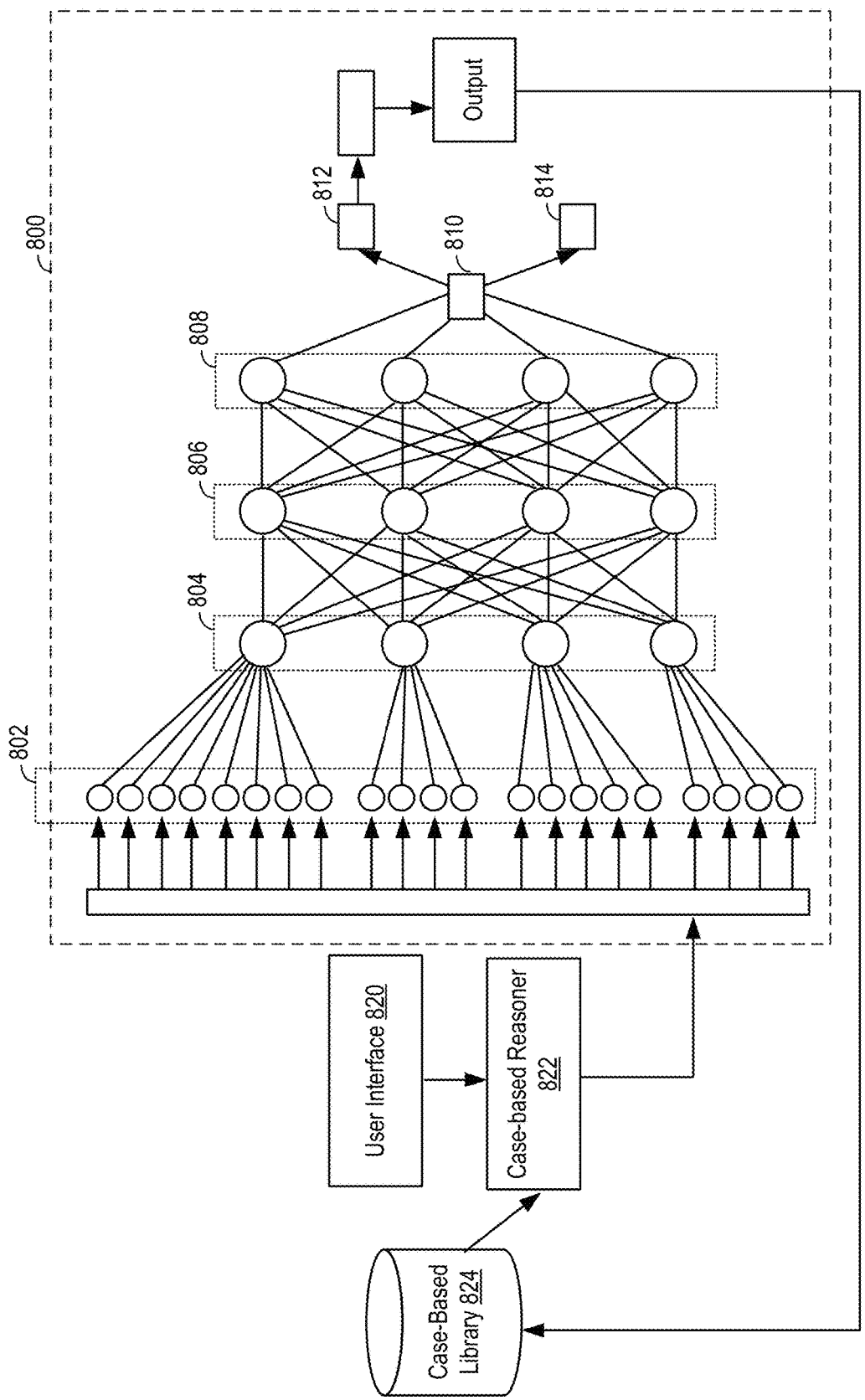
FIG. 8 is a block diagram depicting an example classifier, in accordance with at least one embodiment.

FIG. 8 is a block diagram depicting an example classifier 800, in accordance with at least one embodiment.

The classifier 800 may be an example of a neural network having any suitable number of layers (e.g., layers 802-808).

In some embodiments, a set of observed symptoms of a new case may be provided as input. In some embodiments, this set may be provided via user interface 820. User interface 802 may be an example of the user interface 114 of FIG. 1.

The input may be passed to the case-based reasoner 822. In some embodiments, the case-based reasoner 822 may be configured to perform operations associated with a nearest neighbor algorithm with the input symptoms and a corpus of previously labeled cases from the case-based library 824. In some embodiments, the case-based reasoner 822 may further be configured to compare the new symptoms with all the sets of past confirmed positive and negative case stored in the case-based library for a measure of similarity matching using the Euclidean distance model in a numerical feature space or textual similarity. The case-based reasoner 822 may identify a labeled case that most resembles the symptoms provided as input. If the labeled case includes a measure of similarity match over a threshold degree of similarity with the input symptoms, the most similar case (e.g., a previously identified classification corresponding to the similar case) may be utilized to provide a diagnosis for the input symptoms.

If the most similar case does not exceed some measure of similarity match, the case-based reasoner 822 may be configured to activate a neural network model (e.g., the classifier 800)). The neural network may be previously-trained based on labeled data (e.g., on the cases of case-based library 824 and their corresponding label(s) (e.g., one or more labels indicating a disease, illness, and/or condition associated with the particular case)) to identify a classification (e.g., a disease, illness, and/or condition) for symptoms provided as input. In some embodiments, the input provided to the classifier 800 may include the input symptoms provided to the user interface 820 and symptoms associated with a candidate case of the case-based library 824.

The classifier 800 may include an input layer 802, one or more hidden layers (e.g., layers 804-806) and an output layer (e.g., layer 808). In some embodiments the output layer may output a degree of similarity between the user-provided input symptoms and the symptoms of the candidate case. In some embodiments, if a similarity score provided at 810 indicates the candidate case is not similar (at least not above some predefined similarity threshold), then the case-based reasoner 822 may proceed with activating the classifier 800 with the input symptoms originally provided to user interface 820 and another candidate from the case-based library 824. This process may be performed any suitable number of times.

If the similarity score identified at 810 is above the predefined threshold degree of similarity, as determined at 812, a classification may be identified for the input symptoms (e.g., the classification label associated with the candidate case, which has been determined to exceed the similarity threshold). The classification label(s) of the candidate case may be reused and associated with the input symptoms. The process may proceed to activate a fuzzy logic model 816. The fuzzy logic model 816 may be configured to compute a degree of severity with respect to classification label(s). By way of example, the fuzzy logic model 816 may be configured to take the various parameters identified by the layers 804-806 to identify a severity to be associated with the classification label(s). In some embodiments, the severity may be computed based on computing the following:

$$Y = \sum_{i=1}^{n} L_3(x_i)$$

By way of example, Y can be mapped to an output from a set of outputs such as {mild, moderate, severe}. The diagnosis (e.g., the classification) and the degree of severity may be provided as output and used to update the case-based library 824. In some embodiments, the neural network may be retrained and/or updated with this new case at any suitable time.

Figure 9:
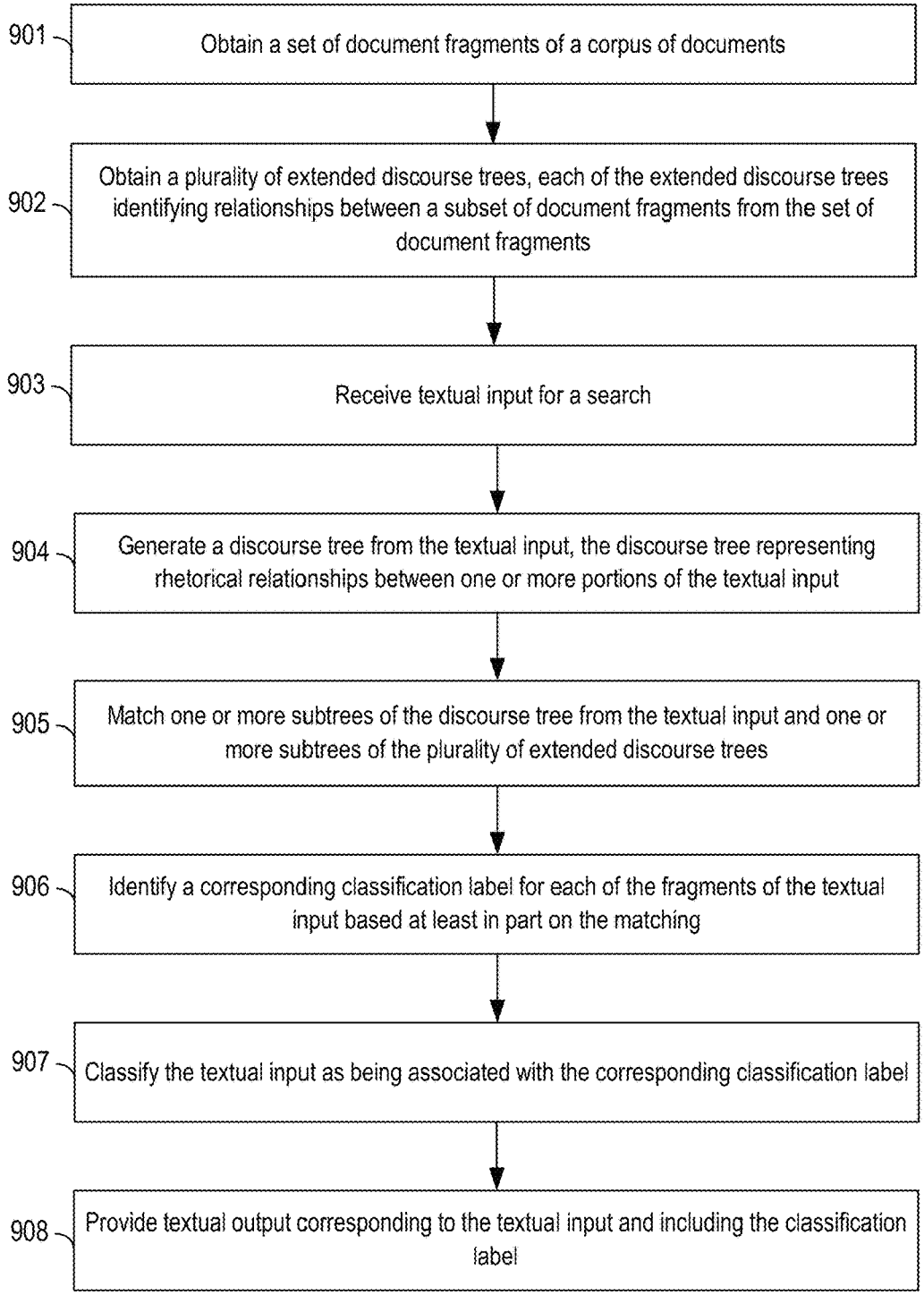
FIG. 9 depicts a flowchart illustrating another example of a method 900 for utilizing multiple previously-classified documents for classifying input, in accordance with at least one embodiment.

FIG. 9 depicts a flowchart illustrating another example of a method 900 for utilizing multiple previously-classified documents for classifying input, in accordance with at least one embodiment. In some embodiments, the method 900 may be performed by the diagnosis engine 402 of FIG. 4 which may operate as part of the autonomous agent application 108 of FIG. 1.

The method 900 may begin at 901, where a set of document fragments of a corpus of documents can be obtained. In some embodiments, each document fragment may be associated with one or more classification labels identifying a topic of the document fragment. By way of example, each document fragment may be associated with a disease, illness, and/or condition corresponding to symptoms the document fragment described.

At 902, a plurality of extended discourse trees may be obtained. In some embodiments, each of the extended discourse trees identify relationships between a subset of document fragments from the set of document fragments. Each extended discourse tree includes at least two discourse trees and each discourse tree includes a plurality of nodes, where each nonterminal node represents a rhetorical relationship between at least two fragments of a corresponding document. In some embodiments, the extended discourse tree indicates one or more rhetorical relationships between the corresponding fragments of the at least two discourse trees, and each terminal node of the nodes of the discourse tree may be associated with one of the fragments. Generation of such discourse trees is described above in connection with FIGS. 5 and 6.

At 903, textual input for a search may be received (e.g., by the autonomous agent application 108. The textual input may be passed to the diagnosis engine 402 of FIG. 4 for processing.

At 904, a discourse tree may be generated (e.g., by the diagnosis engine 402) from the textual input. In some embodiments, the discourse tree represents rhetorical relationships between one or more portions of the textual input.

At 905, one or more subtrees of the discourse tree from the textual input may be matched (e.g., by the diagnosis engine 402) with one or more subtrees of the plurality of extended discourse trees.

At 906, a corresponding classification label may be identified (e.g., by the diagnosis engine 402) for each of the fragments of the textual input based at least in part on the matching.

At 907, the textual input may be classified (e.g., by the diagnosis engine 402) as being associated with the corresponding classification label.

At 908, textual output corresponding to the textual input may be provided (e.g., by the autonomous agent). In some embodiments, the textual output includes the classification label (e.g., the diagnosis).

In some embodiments, method 900 may further comprise parsing (e.g., by the diagnosis engine 402) the textual input to generate an abstract meaning representation of the textual input, the abstract meaning representation comprising a directed acyclic graph including a plurality of nodes and edges, the nodes representing discourse units of the textual input and the edges specifying semantic relationships between the nodes. The method may further include determining (e.g., by the diagnosis engine 402) using an extended discourse tree associated with the set of document fragments and the abstract meaning representation of the input, that the relationships between the fragments of the set of documents agree with the semantic relationships indicated by the abstract meaning representation of the textual input.

In some embodiments, the textual input is classified (e.g., by the diagnosis engine 402) in response to determining that the relationships between the fragments of the set of documents agree with the semantic relationships indicated by the abstract meaning representation of the input.

In some embodiments, the extended discourse trees are generated (e.g., by the diagnosis engine 402) based at least in part on generating a respective discourse tree for each of the set of document fragments, identifying relations between respective pairs of discourse trees, and generating a link between the respective pairs of discourse trees identifying the relations between the respective pairs of discourse trees.

In some embodiments, the plurality of extended discourse trees identify the relationships between the subset of document fragments from the set of document fragments based at least in part on at least one of: a word level, a phrase level, a paragraph level, a sentence level, or a document level.

In some embodiments, the set of documents fragments individually describe symptoms of a respective medical condition.

In some embodiments, the textual input is narrative or structured content from a user's medical file.

In some embodiments, the diagnosis engine 402 may implement the operations described above in connection with FIGS. 7 and 8.

Figure 10:
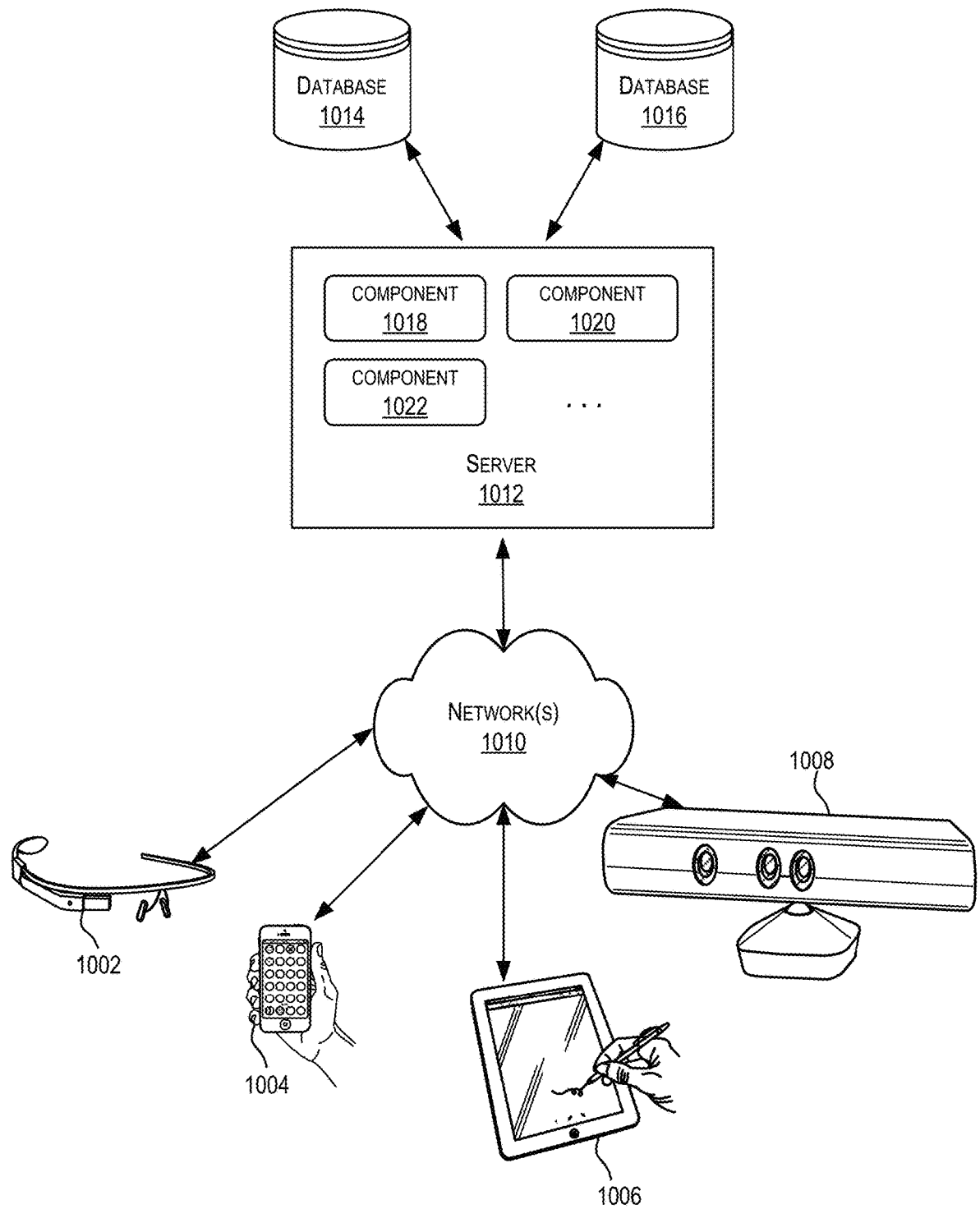
FIG. 10 depicts a simplified diagram of a distributed system for implementing one of the aspects.

FIG. 10 depicts a simplified diagram of a distributed system 1000 for implementing one of the aspects. In the illustrated aspect, distributed system 1000 includes one or more client computing devices 1002, 1004, 1006, and 1008, which are configured to execute and operate a client application such as a web browser, proprietary client (e.g., Oracle Forms), or the like over one or more network(s) 1010. Server 1012 may be communicatively coupled with remote client computing devices 1002, 1004, 1006, and 1008 via network(s) 1010.

In various aspects, server 1012 may be adapted to run one or more services or software applications provided by one or more of the components of the system. The services or software applications can include non-virtual and virtual environments. Virtual environments can include those used for virtual events, tradeshows, simulators, classrooms, shopping exchanges, and enterprises, whether two- or three-dimensional (3D) representations, page-based logical environments, or otherwise. In some aspects, these services may be offered as web-based or cloud services or under a Software as a Service (SaaS) model to the users of client computing devices 1002, 1004, 1006, and/or 1008. Users operating client computing devices 1002, 1004, 1006, and/or 1008 may in turn utilize one or more client applications to interact with server 1012 to utilize the services provided by these components.

In the configuration depicted in the figure, the software components 1018, 1020 and 1022 of system 1000 are shown as being implemented on server 1012. In other aspects, one or more of the components of system 1000 and/or the services provided by these components may also be implemented by one or more of the client computing devices 1002, 1004, 1006, and/or 1008. Users operating the client computing devices may then utilize one or more client applications to use the services provided by these components. These components may be implemented in hardware, firmware, software, or combinations thereof. It should be appreciated that various different system configurations are possible, which may be different from distributed system 1000. The aspect shown in the figure is thus one example of a distributed system for implementing an aspect system and is not intended to be limiting.

Client computing devices 1002, 1004, 1006, and/or 1008 may be portable handheld devices (e.g., an iPhone®, cellular telephone, an iPad®, computing tablet, a personal digital assistant (PDA)) or wearable devices (e.g., a Google Glass® head mounted display), running software such as Microsoft Windows Mobile®, and/or a variety of mobile operating systems such as iOS, Windows Phone, Android, BlackBerry 10, Palm OS, and the like, and being Internet, e-mail, short message service (SMS), Blackberry®, or other communication protocol enabled. The client computing devices can be general purpose personal computers including, by way of example, personal computers and/or laptop computers running various versions of Microsoft Windows®, Apple Macintosh®, and/or Linux operating systems. The client computing devices can be workstation computers running any of a variety of commercially-available UNIX® or UNIX-like operating systems, including without limitation the variety of GNU/Linux operating systems, such as for example, Google Chrome OS. Alternatively, or in addition, client computing devices 1002, 1004, 1006, and 1008 may be any other electronic device, such as a thin-client computer, an Internet-enabled gaming system (e.g., a Microsoft Xbox gaming console with or without a Kinect® gesture input device), and/or a personal messaging device, capable of communicating over network(s) 1010.

Although exemplary distributed system 1000 is shown with four client computing devices, any number of client computing devices may be supported. Other devices, such as devices with sensors, etc., may interact with server 1012.

Network(s) 1010 in distributed system 1000 may be any type of network familiar to those skilled in the art that can support data communications using any of a variety of commercially-available protocols, including without limitation TCP/IP (transmission control protocol/Internet protocol), SNA (systems network architecture), IPX (Internet packet exchange), AppleTalk, and the like. Merely by way of example, network(s) 1010 can be a local area network (LAN), such as one based on Ethernet, Token-Ring and/or the like. Network(s) 1010 can be a wide-area network and the Internet. It can include a virtual network, including without limitation a virtual private network (VPN), an intranet, an extranet, a public switched telephone network (PSTN), an infra-red network, a wireless network (e.g., a network operating under any of the Institute of Electrical and Electronics (IEEE) 802.6 suite of protocols, Bluetooth®, and/or any other wireless protocol); and/or any combination of these and/or other networks.

Server 1012 may be composed of one or more general purpose computers, specialized server computers (including, by way of example, PC (personal computer) servers, UNIX® servers, mid-range servers, mainframe computers, rack-mounted servers, etc.), server farms, server clusters, or any other appropriate arrangement and/or combination. Server 1012 can include one or more virtual machines running virtual operating systems, or other computing architectures involving virtualization. One or more flexible pools of logical storage devices can be virtualized to maintain virtual storage devices for the server. Virtual networks can be controlled by server 1012 using software defined networking. In various aspects, server 1012 may be adapted to run one or more services or software applications described in the foregoing disclosure. For example, server 1012 may correspond to a server for performing processing described above in accordance with an aspect of the present disclosure.

Server 1012 may run an operating system including any of those discussed above, as well as any commercially available server operating system. Server 1012 may also run any of a variety of additional server applications and/or mid-tier applications, including HTTP (hypertext transport protocol) servers, FTP (file transfer protocol) servers, CGI (common gateway interface) servers, JAVA® servers, database servers, and the like. Exemplary database servers include, without limitation, those commercially available from Oracle, Microsoft, Sybase, IBM (International Business Machines), and the like.

In some implementations, server 1012 may include one or more applications to analyze and consolidate data feeds and/or event updates received from users of client computing devices 1002, 1004, 1006, and 1008. As an example, data feeds and/or event updates may include, but are not limited to, Twitter® feeds, Facebook® updates or real-time updates received from one or more third party information sources and continuous data streams, which may include real-time events related to sensor data applications, financial tickers, network performance measuring tools (e.g., network monitoring and traffic management applications), clickstream analysis tools, automobile traffic monitoring, and the like. Server 1012 may also include one or more applications to display the data feeds and/or real-time events via one or more display devices of client computing devices 1002, 1004, 1006, and 1008.

Distributed system 1000 may also include one or more databases 1014 and 1016. Databases 1014 and 1016 may reside in a variety of locations. By way of example, one or more of databases 1014 and 1016 may reside on a non-transitory storage medium local to (and/or resident in) server 1012. Alternatively, databases 1014 and 1016 may be remote from server 1012 and in communication with server 1012 via a network-based or dedicated connection. In one set of aspects, databases 1014 and 1016 may reside in a storage-area network (SAN). Similarly, any necessary files for performing the functions attributed to server 1012 may be stored locally on server 1012 and/or remotely, as appropriate. In one set of aspects, databases 1014 and 1016 may include relational databases, such as databases provided by Oracle, that are adapted to store, update, and retrieve data in response to SQL-formatted commands.

Figure 11:
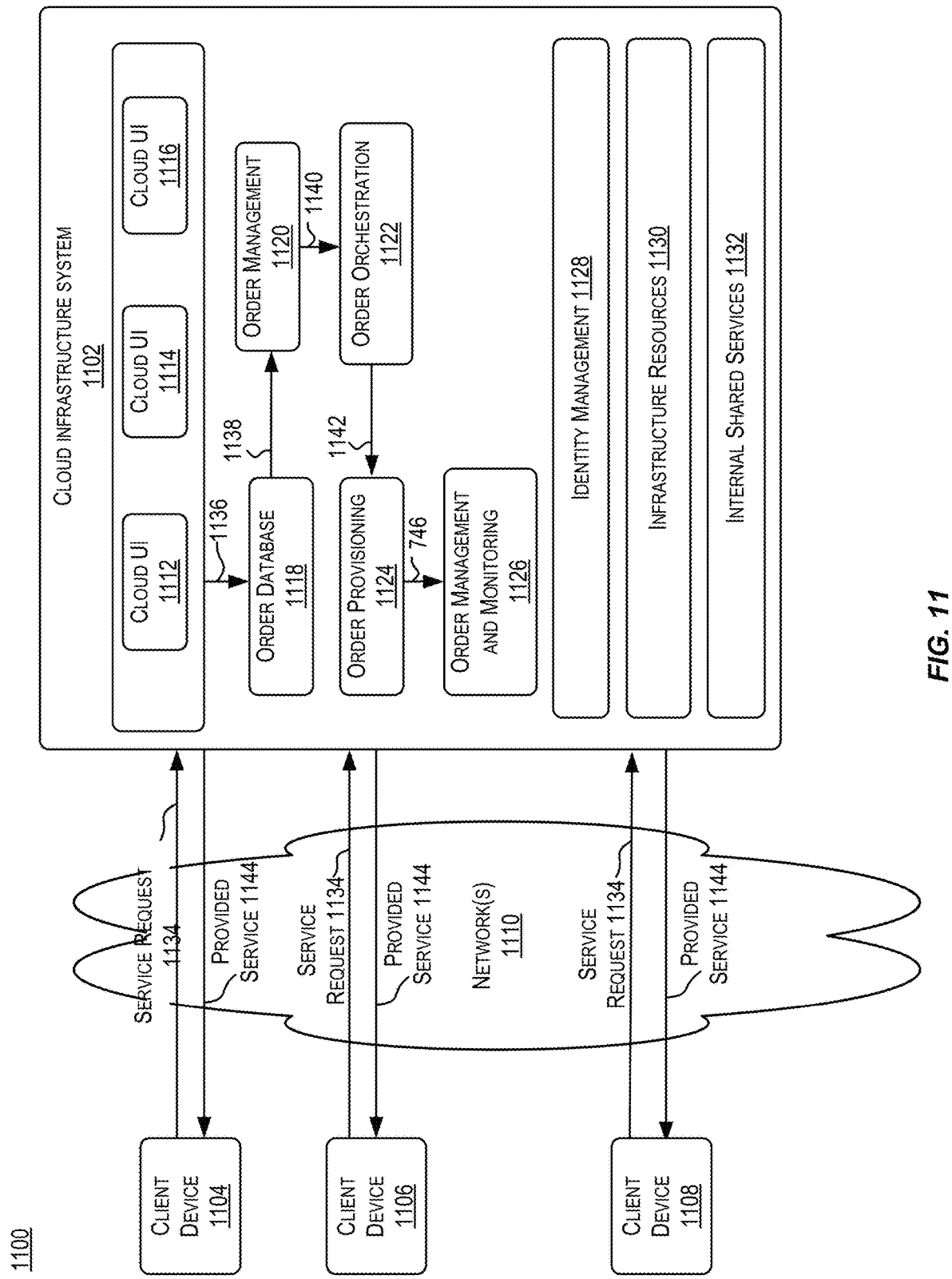
FIG. 11 is a simplified block diagram of components of a system environment by which services provided by the components of an aspect system may be offered as cloud services in accordance with an aspect.

FIG. 11 is a simplified block diagram of one or more components of a system environment 1100 (e.g., a cloud infrastructure system) by which services provided by one or more components of an aspect system may be offered as cloud services, in accordance with an aspect of the present disclosure. In the illustrated aspect, system environment 1100 includes one or more client computing devices 1104, 1106, and 1108 that may be used by users to interact with a cloud infrastructure system 1102 that provides cloud services. The client computing devices may be configured to operate a client application such as a web browser, a proprietary client application (e.g., Oracle Forms), or some other application, which may be used by a user of the client computing device to interact with cloud infrastructure system 1102 to use services provided by cloud infrastructure system 1102.

It should be appreciated that cloud infrastructure system 1102 depicted in the figure may have other components than those depicted. Further, the aspect shown in the figure is only one example of a cloud infrastructure system that may incorporate an aspect of the invention. In some other aspects, cloud infrastructure system 1102 may have more or fewer components than shown in the figure, may combine two or more components, or may have a different configuration or arrangement of components.

Client computing devices 1104, 1106, and 1108 may be devices similar to those described above for 1002, 1004, 1006, and 1008 of FIG. 10.

Although exemplary system environment 1100 is shown with three client computing devices, any number of client computing devices may be supported. Other devices such as devices with sensors, etc. may interact with cloud infrastructure system 1102.

Network(s) 1110 may facilitate communications and exchange of data between client computing devices 1104, 1106, and 1108 and cloud infrastructure system 1102. Each network may be any type of network familiar to those skilled in the art that can support data communications using any of a variety of commercially-available protocols, including those described above for network(s) 1110.

Cloud infrastructure system 1102 may comprise one or more computers and/or servers that may include those described above for server 1012 of FIG. 10.

In certain aspects, services provided by the cloud infrastructure system may include a host of services that are made available to users of the cloud infrastructure system on demand, such as online data storage and backup solutions, Web-based e-mail services, hosted office suites and document collaboration services, database processing, managed technical support services, and the like. Services provided by the cloud infrastructure system can dynamically scale to meet the needs of its users. A specific instantiation of a service provided by cloud infrastructure system is referred to herein as a "service instance." In general, any service made available to a user via a communication network, such as the Internet, from a cloud service provider's system is referred to as a "cloud service." Typically, in a public cloud environment, servers and systems that make up the cloud service provider's system are different from the customer's own on-premises servers and systems. For example, a cloud service provider's system may host an application, and a user may, via a communication network such as the Internet, on demand, order and use the application.

In some examples, a service in a computer network cloud infrastructure may include protected computer network access to storage, a hosted database, a hosted web server, a software application, or other service provided by a cloud vendor to a user, or as otherwise known in the art. For example, a service can include password-protected access to remote storage on the cloud through the Internet. As another example, a service can include a web service-based hosted relational database and a script-language middleware engine for private use by a networked developer. As another example, a service can include access to an email software application hosted on a cloud vendor's web site.

In certain aspects, cloud infrastructure system 1102 may include a suite of applications, middleware, and database service offerings that are delivered to a customer in a self-service, subscription-based, elastically scalable, reliable, highly available, and secure manner. An example of such a cloud infrastructure system is the Oracle Public Cloud provided by the present assignee.

Large volumes of data, sometimes referred to as big data, can be hosted and/or manipulated by the infrastructure system on many levels and at different scales. Such data can include data sets that are so large and complex that it can be difficult to process using typical database management tools or traditional data processing applications. For example, terabytes of data may be difficult to store, retrieve, and process using personal computers or their rack-based counterparts. Such sizes of data can be difficult to work with using most current relational database management systems and desktop statistics and visualization packages. They can require massively parallel processing software running thousands of server computers, beyond the structure of commonly used software tools, to capture, curate, manage, and process the data within a tolerable elapsed time.

Extremely large data sets can be stored and manipulated by analysts and researchers to visualize large amounts of data, detect trends, and/or otherwise interact with the data. Tens, hundreds, or thousands of processors linked in parallel can act upon such data in order to present it or simulate external forces on the data or what it represents. These data sets can involve structured data, such as that organized in a database or otherwise in accordance with a structured model, and/or unstructured data (e.g., emails, images, data blobs (binary large objects), web pages, complex event processing). By leveraging an ability of an aspect to relatively quickly focus more (or fewer) computing resources upon an objective, the cloud infrastructure system may be better available to carry out tasks on large data sets based on demand from a business, government agency, research organization, private individual, group of like-minded individuals or organizations, or other entity.

In various aspects, cloud infrastructure system 1102 may be adapted to automatically provision, manage and track a customer's subscription to services offered by cloud infrastructure system 1102. Cloud infrastructure system 1102 may provide the cloud services via different deployment models. For example, services may be provided under a public cloud model in which cloud infrastructure system 1102 is owned by an organization selling cloud services (e.g., owned by Oracle) and the services are made available to the general public or different industry enterprises. As another example, services may be provided under a private cloud model in which cloud infrastructure system 1102 is operated solely for a single organization and may provide services for one or more entities within the organization. The cloud services may also be provided under a community cloud model in which cloud infrastructure system 1102 and the services provided by cloud infrastructure system 1102 are shared by several organizations in a related community. The cloud services may also be provided under a hybrid cloud model, which is a combination of two or more different models.

In some aspects, the services provided by cloud infrastructure system 1102 may include one or more services provided under a Software as a Service (SaaS) category, Platform as a Service (PaaS) category, Infrastructure as a Service (IaaS) category, or other categories of services including hybrid services. A customer, via a subscription order, may order one or more services provided by cloud infrastructure system 1102. Cloud infrastructure system 1102 then performs processing to provide the services in the customer's subscription order.

In some aspects, the services provided by cloud infrastructure system 1102 may include, without limitation, application services, platform services and infrastructure services. In some examples, application services may be provided by the cloud infrastructure system via a SaaS platform. The SaaS platform may be configured to provide cloud services that fall under the SaaS category. For example, the SaaS platform may provide capabilities to build and deliver a suite of on-demand applications on an integrated development and deployment platform. The SaaS platform may manage and control the underlying software and infrastructure for providing the SaaS services. By utilizing the services provided by the SaaS platform, customers can utilize applications executing on the cloud infrastructure system. Customers can acquire the application services without the need for customers to purchase separate licenses and support. Various different SaaS services may be provided. Examples include, without limitation, services that provide solutions for sales performance management, enterprise integration, and business flexibility for large organizations.

In some aspects, platform services may be provided by the cloud infrastructure system via a PaaS platform. The PaaS platform may be configured to provide cloud services that fall under the PaaS category. Examples of platform services may include, without limitation, services that enable organizations (such as Oracle) to consolidate existing applications on a shared, common architecture, as well as the ability to build new applications that leverage the shared services provided by the platform. The PaaS platform may manage and control the underlying software and infrastructure for providing the PaaS services. Customers can acquire the PaaS services provided by the cloud infrastructure system without the need for customers to purchase separate licenses and support. Examples of platform services include, without limitation, Oracle Java Cloud Service (JCS), Oracle Database Cloud Service (DBCS), and others.

By utilizing the services provided by the PaaS platform, customers can employ programming languages and tools supported by the cloud infrastructure system and also control the deployed services. In some aspects, platform services provided by the cloud infrastructure system may include database cloud services, middleware cloud services (e.g., Oracle Fusion Middleware services), and Java cloud services. In one aspect, database cloud services may support shared service deployment models that enable organizations to pool database resources and offer customers a Database as a Service in the form of a database cloud. Middleware cloud services may provide a platform for customers to develop and deploy various business applications, and Java cloud services may provide a platform for customers to deploy Java applications, in the cloud infrastructure system.

Various different infrastructure services may be provided by an IaaS platform in the cloud infrastructure system. The infrastructure services facilitate the management and control of the underlying computing resources, such as storage, networks, and other fundamental computing resources for customers utilizing services provided by the SaaS platform and the PaaS platform.

In certain aspects, cloud infrastructure system 1102 may also include infrastructure resources 1130 for providing the resources used to provide various services to customers of the cloud infrastructure system. In one aspect, infrastructure resources 1130 may include pre-integrated and optimized combinations of hardware, such as servers, storage, and networking resources to execute the services provided by the PaaS platform and the SaaS platform.

In some aspects, resources in cloud infrastructure system 1102 may be shared by multiple users and dynamically re-allocated per demand. Additionally, resources may be allocated to users in different time zones. For example, cloud infrastructure system 1102 may enable a first set of users in a first time zone to utilize resources of the cloud infrastructure system for a specified number of hours and then enable the re-allocation of the same resources to another set of users located in a different time zone, thereby maximizing the utilization of resources.

In certain aspects, a number of internal shared services 1132 may be provided that are shared by different components or modules of cloud infrastructure system 1102 and by the services provided by cloud infrastructure system 1102. These internal shared services may include, without limitation, a security and identity service, an integration service, an enterprise repository service, an enterprise manager service, a virus scanning and white list service, a high availability, backup and recovery service, service for enabling cloud support, an email service, a notification service, a file transfer service, and the like.

In certain aspects, cloud infrastructure system 1102 may provide comprehensive management of cloud services (e.g., SaaS, PaaS, and IaaS services) in the cloud infrastructure system. In one aspect, cloud management functionality may include capabilities for provisioning, managing and tracking a customer's subscription received by cloud infrastructure system 1102, and the like.

In one aspect, as depicted in the figure, cloud management functionality may be provided by one or more modules, such as an order management module 1120, an order orchestration module 1122, an order provisioning module 1124, an order management and monitoring module 1126, and an identity management module 1128. These modules may include or be provided using one or more computers and/or servers, which may be general purpose computers, specialized server computers, server farms, server clusters, or any other appropriate arrangement and/or combination.

In exemplary operation 1134, a customer using a client device, such as client computing devices 1104, 1106 or 1108, may interact with cloud infrastructure system 1102 by requesting one or more services provided by cloud infrastructure system 1102 and placing an order for a subscription for one or more services offered by cloud infrastructure system 1102. In certain aspects, the customer may access a cloud User Interface (UI), cloud UI 1112, cloud UI 1114 and/or cloud UI 1116 and place a subscription order via these UIs. The order information received by cloud infrastructure system 1102 in response to the customer placing an order may include information identifying the customer and one or more services offered by the cloud infrastructure system 1102 in which the customer intends to subscribe.

After an order has been placed by the customer, the order information is received via the cloud UIs, 1112, 1114 and/or 1116.

At operation 1136, the order is stored in order database 1118. Order database 1118 can be one of several databases operated by cloud infrastructure system 1102 and operated in conjunction with other system elements.

At operation 1138, the order information is forwarded to an order management module 1120. In some instances, order management module 1120 may be configured to perform billing and accounting functions related to the order, such as verifying the order, and upon verification, booking the order.

At operation 1140, information regarding the order is communicated to an order orchestration module 1122. Order orchestration module 1122 may utilize the order information to orchestrate the provisioning of services and resources for the order placed by the customer. In some instances, order orchestration module 1122 may orchestrate the provisioning of resources to support the subscribed services using the services of order provisioning module 1124.

In certain aspects, order orchestration module 1122 enables the management of business processes associated with each order and applies business logic to determine whether an order should proceed to provisioning. At operation 1142, upon receiving an order for a new subscription, order orchestration module 1122 sends a request to order provisioning module 1124 to allocate resources and configure those resources needed to fulfill the subscription order. Order provisioning module 1124 enables the allocation of resources for the services ordered by the customer. Order provisioning module 1124 provides a level of abstraction between the cloud services provided by system environment 1100 and the physical implementation layer that is used to provision the resources for providing the requested services. Order orchestration module 1122 may thus be isolated from implementation details, such as whether or not services and resources are actually provisioned on the fly or pre-provisioned and only allocated/assigned upon request.

At operation 1144, once the services and resources are provisioned, a notification of the provided service may be sent to customers on client computing devices 1104, 1106 and/or 1108 by order provisioning module 1124 of cloud infrastructure system 1102.

At operation 1146, the customer's subscription order may be managed and tracked by an order management and monitoring module 1126. In some instances, order management and monitoring module 1126 may be configured to collect usage statistics for the services in the subscription order, such as the amount of storage used, the amount data transferred, the number of users, and the amount of system up time and system down time.

In certain aspects, system environment 1100 may include an identity management module 1128. Identity management module 1128 may be configured to provide identity services, such as access management and authorization services in system environment 1100. In some aspects, identity management module 1128 may control information about customers who wish to utilize the services provided by cloud infrastructure system 1102. Such information can include information that authenticates the identities of such customers and information that describes which actions those customers are authorized to perform relative to various system resources (e.g., files, directories, applications, communication ports, memory segments, etc.). Identity management module 1128 may also include the management of descriptive information about each customer and about how and by whom that descriptive information can be accessed and modified.

Figure 12:
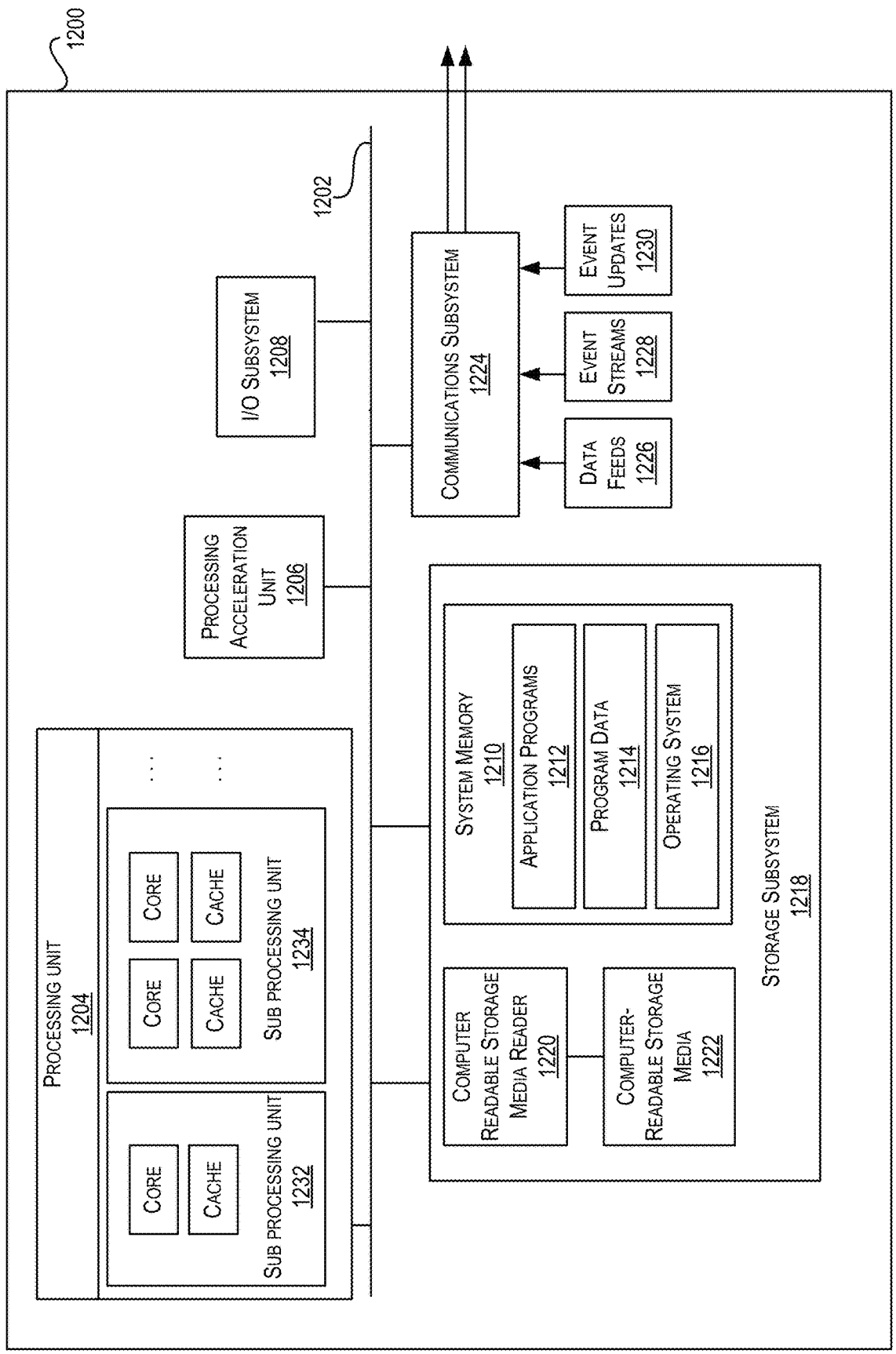
FIG. 12 illustrates an exemplary computer system, in which various aspects may be implemented.

FIG. 12 illustrates an exemplary computer system 1200, in which various aspects may be implemented. The system 1200 may be used to implement any of the computer systems described above. As shown in the figure, computer system 1200 includes a processing unit 1204 that communicates with a number of peripheral subsystems via a bus subsystem 1202. These peripheral subsystems may include a processing acceleration unit 1206, an I/O subsystem 1208, a storage subsystem 1218 and a communications subsystem 1224. Storage subsystem 1218 includes tangible computer-readable storage media 1222 and a system memory 1210.

Bus subsystem 1202 provides a mechanism for letting the various components and subsystems of computer system 1200 communicate with each other as intended. Although bus subsystem 1202 is shown schematically as a single bus, alternative aspects of the bus subsystem may utilize multiple buses. Bus subsystem 1202 may be any of several types of bus structures including a memory bus or memory controller, a peripheral bus, and a local bus using any of a variety of bus architectures. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P886.1 standard.

Processing unit 1204, which can be implemented as one or more integrated circuits (e.g., a conventional microprocessor or microcontroller), controls the operation of computer system 1200. One or more processors may be included in processing unit 1204. These processors may include single core or multicore processors. In certain aspects, processing unit 1204 may be implemented as one or more independent processing units 1232 and/or 1234 with single or multicore processors included in each processing unit. In other aspects, processing unit 1204 may also be implemented as a quad-core processing unit formed by integrating two dual-core processors into a single chip.

In various aspects, processing unit 1204 can execute a variety of programs in response to program code and can maintain multiple concurrently executing programs or processes. At any given time, some or all of the program code to be executed can be resident in processing unit 1204 and/or in storage subsystem 1218. Through suitable programming, processing unit 1204 can provide various functionalities described above. Computer system 1200 may additionally include a processing acceleration unit 1206, which can include a digital signal processor (DSP), a special-purpose processor, and/or the like.

I/O subsystem 1208 may include user interface input devices and user interface output devices. User interface input devices may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may include, for example, motion sensing and/or gesture recognition devices such as the Microsoft Kinect® motion sensor that enables users to control and interact with an input device, such as the Microsoft Xbox® 360 game controller, through a natural user interface using gestures and spoken commands. User interface input devices may also include eye gesture recognition devices such as the Google Glass® blink detector that detects eye activity (e.g., 'blinking' while taking pictures and/or making a menu selection) from users and transforms the eye gestures as input into an input device (e.g., Google Glass®). Additionally, user interface input devices may include voice recognition sensing devices that enable users to interact with voice recognition systems (e.g., Siri® navigator), through voice commands.

User interface input devices may also include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, medical ultrasonography devices. User interface input devices may also include, for example, audio input devices such as MIDI keyboards, digital musical instruments and the like.

User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. In general, use of the term "output device" is intended to include all possible types of devices and mechanisms for outputting information from computer system 1200 to a user or other computer. For example, user interface output devices may include, without limitation, a variety of display devices that visually convey text, graphics and audio/video information such as monitors, printers, speakers, headphones, automotive navigation systems, plotters, voice output devices, and modems.

Computer system 1200 may comprise a storage subsystem 1218 that comprises software elements, shown as being currently located within a system memory 1210. System memory 1210 may store program instructions that are loadable and executable on processing unit 1204, as well as data generated during the execution of these programs.

Depending on the configuration and type of computer system 1200, system memory 1210 may be volatile (such as random access memory (RAM)) and/or non-volatile (such as read-only memory (ROM), flash memory, etc.) The RAM typically contains data and/or program modules that are immediately accessible to and/or presently being operated and executed by processing unit 1204. In some implementations, system memory 1210 may include multiple different types of memory, such as static random access memory (SRAM) or dynamic random access memory (DRAM). In some implementations, a basic input/output system (BIOS), containing the basic routines that help to transfer information between elements within computer system 1200, such as during start-up, may typically be stored in the ROM. By way of example, and not limitation, system memory 1210 also illustrates application programs 1212, which may include client applications, Web browsers, mid-tier applications, relational database management systems (RDBMS), etc., program data 1214, and an operating system 1216. By way of example, operating system 1216 may include various versions of Microsoft Windows®, Apple Macintosh®, and/or Linux operating systems, a variety of commercially-available UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® 10 OS, and Palm® OS operating systems.

Storage subsystem 1218 may also provide a tangible computer-readable storage medium for storing the basic programming and data constructs that provide the functionality of some aspects. Software (programs, code modules, instructions) that when executed by a processor provide the functionality described above, may be stored in storage subsystem 1218. These software modules or instructions may be executed by processing unit 1204. Storage subsystem 1218 may also provide a repository for storing data used in accordance with the present invention.

Storage subsystem 1218 may also include a computer-readable storage media reader 1220 that can further be connected to computer-readable storage media 1222. Together and, optionally, in combination with system memory 1210, computer-readable storage media 1222 may comprehensively represent remote, local, fixed, and/or removable storage devices plus storage media for temporarily and/or more permanently containing, storing, transmitting, and retrieving computer-readable information.

Computer-readable storage media 1222 containing code, or portions of code, can also include any appropriate media known or used in the art, including storage media and communication media such as, but not limited to, volatile and non-volatile, removable and non-removable media implemented in any method or technology for storage and/or transmission of information. This can include tangible, non-transitory computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. When specified, this can also include nontangible, transitory computer-readable media, such as data signals, data transmissions, or any other medium which can be used to transmit the desired information and which can be accessed by computing system 1200.

By way of example, computer-readable storage media 1222 may include a hard disk drive that reads from or writes to non-removable, non-volatile magnetic media, a magnetic disk drive that reads from or writes to a removable, non-volatile magnetic disk, and an optical disk drive that reads from or writes to a removable, non-volatile optical disk such as a CD ROM, DVD, and Blu-Ray® disk, or other optical media. Computer-readable storage media 1222 may include, but is not limited to, Zip® drives, flash memory cards, universal serial bus (USB) flash drives, secure digital (SD) cards, DVD disks, digital video tape, and the like. Computer-readable storage media 1222 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 1200.

Communications subsystem 1224 provides an interface to other computer systems and networks. Communications subsystem 1224 serves as an interface for receiving data from and transmitting data to other systems from computer system 1200. For example, communications subsystem 1224 may enable computer system 1200 to connect to one or more devices via the Internet. In some aspects, communications subsystem 1224 can include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.28 family standards, or other mobile communication technologies, or any combination thereof), global positioning system (GPS) receiver components, and/or other components. In some aspects, communications subsystem 1224 can provide wired network connectivity (e.g., Ethernet) in addition to or instead of a wireless interface.

In some aspects, communications subsystem 1224 may also receive input communication in the form of structured and/or unstructured data feeds 1226, event streams 1228, event updates 1230, and the like on behalf of one or more users who may use computer system 1200.

By way of example, communications subsystem 1224 may be configured to receive unstructured data feeds 1226 in real-time from users of social media networks and/or other communication services such as Twitter® feeds, Facebook® updates, web feeds such as Rich Site Summary (RSS) feeds, and/or real-time updates from one or more third party information sources.

Additionally, communications subsystem 1224 may also be configured to receive data in the form of continuous data streams, which may include event streams 1228 of real-time events and/or event updates 1230, that may be continuous or unbounded in nature with no explicit end. Examples of applications that generate continuous data may include, for example, sensor data applications, financial tickers, network performance measuring tools (e.g. network monitoring and traffic management applications), clickstream analysis tools, automobile traffic monitoring, and the like.

Communications subsystem 1224 may also be configured to output the structured and/or unstructured data feeds 1226, event streams 1228, event updates 1230, and the like to one or more databases that may be in communication with one or more streaming data source computers coupled to computer system 1200.

Computer system 1200 can be one of various types, including a handheld portable device (e.g., an iPhone® cellular phone, an iPad® computing tablet, a PDA), a wearable device (e.g., a Google Glass® head mounted display), a PC, a workstation, a mainframe, a kiosk, a server rack, or any other data processing system.

Due to the ever-changing nature of computers and networks, the description of computer system 1200 depicted in the figure is intended only as a specific example. Many other configurations having more or fewer components than the system depicted in the figure are possible. For example, customized hardware might also be used and/or particular elements might be implemented in hardware, firmware, software (including applets), or a combination. Further, connection to other computing devices, such as network input/output devices, may be employed. Based on the disclosure and teachings provided herein, a person of ordinary skill in the art will appreciate other ways and/or methods to implement the various aspects.

In the foregoing specification, aspects of the invention are described with reference to specific aspects thereof, but those skilled in the art will recognize that the invention is not limited thereto. Various attributes and aspects of the above-described invention may be used individually or jointly. Further, aspects can be utilized in any number of environments and applications beyond those described herein without departing from the broader spirit and scope of the specification. The specification and drawings are, accordingly, to be regarded as illustrative rather than restrictive.

What is claimed is:

1. A computer-implemented method for utilizing multi-case based reasoning to generate an automated diagnosis, comprising:

obtaining, by one or more processors, a set of document fragments of a corpus of documents, each document fragment being associated with one or more classification labels identifying a diagnosis of the document fragment;

obtaining, by the one or more processors, a plurality of extended discourse trees, each of the extended discourse trees identifying rhetorical relationships between a subset of document fragments from the set of document fragments, each extended discourse tree including at least two discourse trees, each discourse tree including a plurality of nodes, each nonterminal node representing a rhetorical relationship between at least two sub-fragments of a corresponding document fragment, and each terminal node of the nodes of the discourse tree being associated with one of the sub-fragments;

receiving, by the one or more processors, a diagnosis request comprising textual input indicating one or more symptoms;

generating, by the one or more processors, a discourse tree from the textual input, the discourse tree representing first rhetorical relationships between the one or more symptoms of the textual input;

identifying, by the one or more processors, one or more subtrees of the plurality of extended discourse trees corresponding to one or more document fragments based on the discourse tree that was generated from the textual input;

determining, by the one or more processors, that second rhetorical relationships between the one or more subtrees of the plurality of extended discourse trees match the first rhetorical relationships between the one or more symptoms indicated in the textual input;

based at least in part on determining the match, identifying one or more diagnosis labels for each of the one or more symptoms of the textual input from corresponding diagnosis labels individually associated with the one or more document fragments;

classifying, utilizing a neural network, the textual input as being associated with at least one diagnosis label, wherein classifying the textual input comprises providing the one or more symptoms to the neural network as input and receiving output from the neural network that indicates the at least one diagnosis label; and providing output corresponding to the text input and comprising the automated diagnosis, the automated diagnosis including the one or more diagnosis labels identified by matching each of the one or more symptoms to the one or more document fragments and the at least one diagnosis label identified by the output from the neural network.

2. The computer-implemented method of claim 1, further comprising:

parsing the textual input to generate an abstract meaning representation of the textual input, the abstract meaning representation comprising a directed acyclic graph including a corresponding plurality of nodes and edges, the nodes representing discourse units of the textual input and the edges specifying semantic relationships between the nodes; and determining, by the one or more processors, using an extended discourse tree of the plurality of extended discourse trees and the abstract meaning representation of the input, that relationships between document fragments of the set of documents fragments agree with the semantic relationships indicated by the abstract meaning representation of the textual input.

3. The computer-implemented method of claim 2, wherein identifying the one or more diagnosis labels for each of the one or more symptoms is based at least in part on determining that the relationships between the one or more document fragments of the set of documents fragments agree with the semantic relationships indicated by the abstract meaning representation of the input.

4. The computer-implemented method of claim 1, wherein the extended discourse trees are generated based at least in part on generating a respective discourse tree for each of the set of document fragments, identifying respective rhetorical relationships between respective pairs of discourse trees, and generating a link between the respective pairs of discourse trees identifying the respective rhetorical relationships between the respective pairs of discourse trees.

5. The computer-implemented method of claim 1, wherein the plurality of extended discourse trees identify respective rhetorical relationships between the subset of document fragments from the set of document fragments based at least in part on at least one of: a word level, a phrase level, a paragraph level, a sentence level, or a document level.

6. The computer-implemented method of claim 1, wherein the textual input is narrative or structured content from a user's medical file.

7. The computer-implemented method of claim 1, wherein the neural network is previously trained utilizing a supervised learning algorithm and a training data set comprising a plurality of examples for which a set of one or more diagnosis labels are known, an example of the plurality of examples comprising a set of one or more symptoms, diagnosis labels corresponding to a document of the corpus of documents, and the set of one or more diagnosis labels that are identified as corresponding to the set of one or more symptoms, the neural network being configured to receive the one or more symptoms of the diagnosis request and provide as output the at least one diagnosis label identified for the one or more symptoms from the diagnosis labels corresponding to the corpus of documents.

8. A computing device, comprising:
one or more processors; and
one or more memories storing computer-readable instructions for utilizing multi-case based reasoning to generate an automated diagnosis, that, when executed by the one or more processors, cause the computing device to perform operations comprising:

obtaining a set of document fragments of a corpus of documents, each document fragment being associated with one or more classification labels identifying a diagnosis of the document fragment;

obtaining a plurality of extended discourse trees, each of the extended discourse trees identifying rhetorical relationships between a subset of document fragments from the set of document fragments, each extended discourse tree including at least two discourse trees, each discourse tree including a plurality of nodes, each nonterminal node representing a rhetorical relationship between at least two sub-fragments of a corresponding document fragment, the extended discourse tree indicating one or more rhetorical relationships between and each terminal node of the nodes of the discourse tree being associated with one of the sub-fragments;

receiving by the one or more processors, a diagnosis request comprising textual input indicating one or more symptoms;

generating a discourse tree from the textual input, the discourse tree representing first rhetorical relationships between the one or more symptoms of the textual input;

identifying one or more subtrees of the plurality of extended discourse trees corresponding to one or more document fragments based on the discourse tree that was generated from the textual input;

determining that second rhetorical relationships between the one or more subtrees of the plurality of extended discourse trees match the first rhetorical relationships between the one or more symptoms indicated in the textual input;

based at least in part on determining the match, identifying one or more diagnosis labels for each of the one or more symptoms of the textual input from corresponding diagnosis labels individually associated with the one or more document fragments;

classifying, utilizing a neural network, the textual input as being associated with at least one diagnosis label, wherein classifying the textual input comprises providing the one or more symptoms to the neural network as input and receiving output from the neural network that indicates the at least one diagnosis label; and providing output corresponding to the textual input and comprising the automated diagnosis, the automated diagnosis including the one or more diagnosis labels identified by matching each of the one or more symptoms to the one or more document fragments and the at least one diagnosis label identified by the output from the neural network.

9. The computing device of claim 8, wherein the operations further comprise:

parsing the textual input to generate an abstract meaning representation of the textual input, the abstract meaning representation comprising a directed acyclic graph including a corresponding plurality of nodes and edges, the nodes representing discourse units of the textual input and the edges specifying semantic relationships between the nodes; and determining, by the one or more processors, using an extended discourse tree of the plurality of extended discourse trees and the abstract meaning representation of the input, that relationships between document fragments of the set of documents fragments agree with the semantic relationships indicated by the abstract meaning representation of the textual input.

10. The computing device of claim 9, wherein identifying the one or more diagnosis labels for each of the one or more symptoms is based at least in part on determining that the relationships between the one or more document fragments of the set of documents fragments agree with the semantic relationships indicated by the abstract meaning representation of the input.

11. The computing device of claim 8, wherein the extended discourse trees are generated based at least in part on generating a respective discourse tree for each of the set of document fragments, identifying respective rhetorical relationships between respective pairs of discourse trees, and generating a link between the respective pairs of discourse trees identifying the respective rhetorical relationships between the respective pairs of discourse trees.

12. The computing device of claim 8, wherein the plurality of extended discourse trees identify respective rhetorical relationships between the subset of document fragments of the set of document fragments based at least in part on at least one of: a word level, a phrase level, a paragraph level, a sentence level, or a document level.

13. The computing device of claim 8, wherein the textual input is narrative or structured content from a user's medical file.

14. The computing device of claim 8, wherein the neural network is previously trained utilizing a supervised learning algorithm and a training data set comprising a plurality of examples for which a set of one or more diagnosis labels are known, an example of the plurality of examples comprising a set of one or more symptoms, diagnosis labels corresponding to a document of the corpus of documents, and the set of one or more diagnosis labels that are identified as corresponding to the set of one or more symptoms, the neural network being configured to receive the one or more symptoms of the diagnosis request and provide as output the at least one diagnosis label identified for the one or more symptoms from the diagnosis labels corresponding to the corpus of documents.

15. A non-transitory computer-readable storage medium comprising computer-readable instructions for utilizing multi-case based reasoning to generate an automated diagnosis, that, when executed by one or more processors of a computing device, cause the computing device to perform operations comprising:
obtaining a set of document fragments of a corpus of documents, each document fragment being associated with one or more classification labels identifying a diagnosis of the document fragment;
obtaining a plurality of extended discourse trees, each of the extended discourse trees identifying rhetorical relationships between a subset of document fragments from the set of document fragments, each extended discourse tree including at least two discourse trees, each discourse tree including a plurality of nodes, each nonterminal node representing a rhetorical relationship between at least two sub-fragments of a corresponding document fragment, and each terminal node of the nodes of the discourse tree being associated with one of the sub-fragments;
receiving by the one or more processors, a diagnosis request comprising textual input indicating one or more symptoms;
generating a discourse tree from the textual input, the discourse tree representing first rhetorical relationships between the one or more symptoms of the textual input;
identifying one or more subtrees of the plurality of extended discourse trees corresponding to one or more document fragments based on the discourse tree that was generated from the textual input;
determining that second rhetorical relationships between the one or more subtrees of the plurality of extended discourse trees match the first rhetorical relationships between the one or more symptoms indicated in the textual input;
based at least in part on determining the match, identifying one or more diagnosis labels for each of the one or more symptoms of the textual input from corresponding diagnosis labels individually associated with the one or more document fragments;
classifying, utilizing a neural network, the textual input as being associated with at least one diagnosis label, wherein classifying the textual input comprises providing the one or more symptoms to the neural network as input and receiving output from the neural network that indicates the at least one diagnosis label; and
providing output corresponding to the textual input and comprising the automated diagnosis, the automated diagnosis including the one or more diagnosis labels identified by matching each of the one or more symptoms to the one or more document fragments and the at least one diagnosis label identified by the output from the neural network.

16. The non-transitory computer-readable storage medium of claim 15, wherein the operations further comprise:
parsing the textual input to generate an abstract meaning representation of the textual input, the abstract meaning representation comprising a directed acyclic graph including a corresponding plurality of nodes and edges, the nodes representing discourse units of the textual input and the edges specifying semantic relationships between the nodes; and
determining, by the one or more processors, using an extended discourse tree of the plurality of extended discourse trees and the abstract meaning representation of the input, that relationships between document fragments of the set of documents fragments agree with the semantic relationships indicated by the abstract meaning representation of the textual input.

17. The non-transitory computer-readable storage medium of claim 16, wherein identifying the one or more diagnosis labels for each of the one or more symptoms is based at least in part on determining that the relationships between the one or more document fragments of the set of documents fragments agree with the semantic relationships indicated by the abstract meaning representation of the input.

18. The non-transitory computer-readable storage medium of claim 15, wherein the extended discourse trees are generated based at least in part on generating a respective discourse tree for each of the set of document fragments, identifying respective rhetorical relationships between respective pairs of discourse trees, and generating a link between the respective pairs of discourse trees identifying the respective rhetorical relationships between the respective pairs of discourse trees.

19. The non-transitory computer-readable storage medium of claim 15, wherein the plurality of extended discourse trees identify respective rhetorical relationships between the subset of document fragments from the set of document fragments based at least in part on at least one of: a word level, a phrase level, a paragraph level, a sentence level, or a document level.

20. The non-transitory computer-readable storage medium of claim 15, wherein the neural network is previously trained utilizing a supervised learning algorithm and a training data set comprising a plurality of examples for which a set of one or more diagnosis labels are known, an example of the plurality of examples comprising a set of one or more symptoms, diagnosis labels corresponding to a document of the corpus of documents, and the set of one or more diagnosis labels that are identified as corresponding to the set of one or more symptoms, the neural network being configured to receive the one or more symptoms of the diagnosis request and provide as output the at least one diagnosis label identified for the one or more symptoms from the diagnosis labels corresponding to the corpus of documents.

* * * * *